United States Patent
Epstein et al.

(10) Patent No.: US 10,479,986 B2
(45) Date of Patent: Nov. 19, 2019

(54) NUCLEIC ACID CONSTRUCTS AND METHODS FOR LABELING AND DETECTING NUCLEOSOMAL DNA MODIFICATIONS

(71) Applicants: THE BROAD INSTITUTE, INC., Cambridge, MA (US); THE GENERAL HOSPITAL CORPORATION, Boston, MA (US)

(72) Inventors: Charles B. Epstein, Brookline, MA (US); Peter Van Galen, Boston, MA (US); Bradley E. Bernstein, Cambridge, MA (US)

(73) Assignees: The Broad Institute, Inc., Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/607,244

(22) Filed: May 26, 2017

(65) Prior Publication Data

US 2017/0343539 A1 Nov. 30, 2017

Related U.S. Application Data

(60) Provisional application No. 62/342,439, filed on May 27, 2016.

(51) Int. Cl.
| | | |
|---|---|---|
| *C12N 9/64* | (2006.01) | |
| *C12N 15/52* | (2006.01) | |
| *C12Q 1/6804* | (2018.01) | |
| *C12Q 1/6806* | (2018.01) | |
| *C12Q 1/6869* | (2018.01) | |
| *G01N 33/00* | (2006.01) | |

(52) U.S. Cl.
CPC .............. *C12N 9/64* (2013.01); *C12N 15/52* (2013.01); *C12Q 1/6804* (2013.01); *C12Q 1/6806* (2013.01); *C12Q 1/6869* (2013.01); *G01N 33/00* (2013.01)

(58) Field of Classification Search
None
See application file for complete search history.

(56) References Cited

FOREIGN PATENT DOCUMENTS

WO    WO 2017/034970 A1 * 3/2017    ........... C12Q 1/6883

* cited by examiner

*Primary Examiner* — Nancy J Leith
(74) *Attorney, Agent, or Firm* — Johnson, Marcou & Isaacs, LLC

(57) ABSTRACT

Embodiments disclosed herein provide methods for identifying cell-type-specific nucleosomal DNA modifications. The methods leverage nucleosomal DNA barcoding and pool-and-split multiplexing to provide high-throughout, quantitative profiling of nucleosomal DNA states. The methods enable the profiling of multiple nucleosomal DNA marks across different cell types and/or conditions thereby linking quantitative changes in chromatin landscapes to different genotypes and chemical and physical perturbations.

14 Claims, 29 Drawing Sheets

Specification includes a Sequence Listing.

① Lysis + MNase digestion
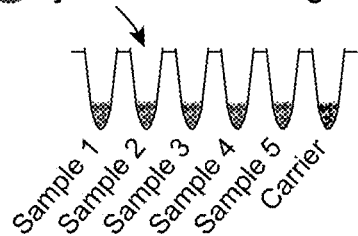
② Adapter ligation
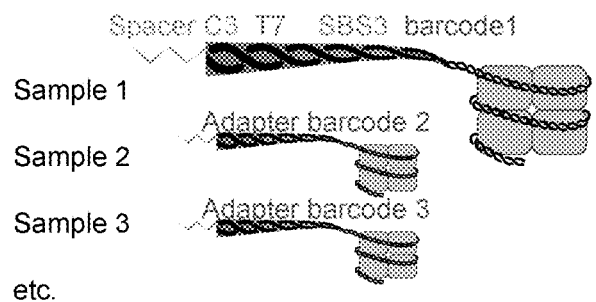
Sample 1
Sample 2
Sample 3
etc.
③ Mix and split samples for ChIP
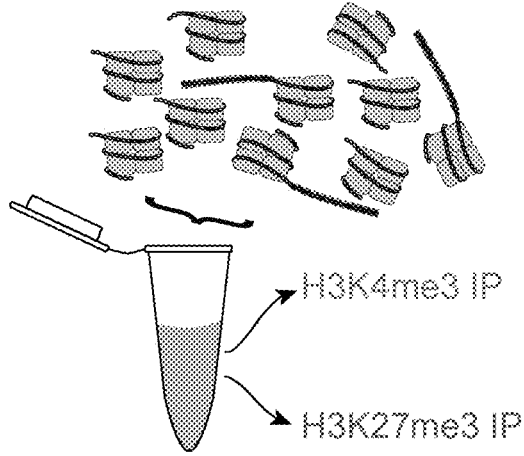
H3K4me3 IP
H3K27me3 IP
FIG. 1

① Adapter-ligated DNA after immunoprecipitation
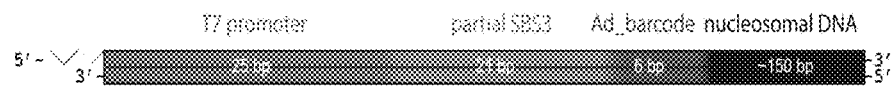
② Reverse transcription (RNA → cDNA)
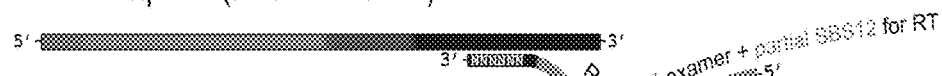
③ Nested library PCR
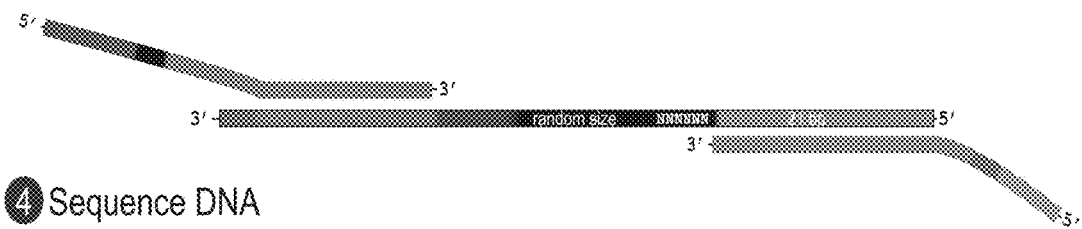
④ Sequence DNA
FIG. 2

1. Adapter-ligated DNA after immunoprecipitation
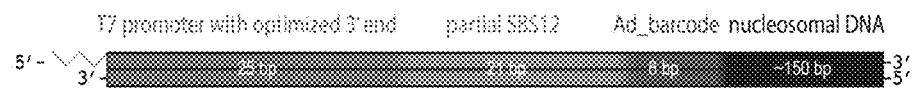
2. Reverse transcription (RNA → cDNA)
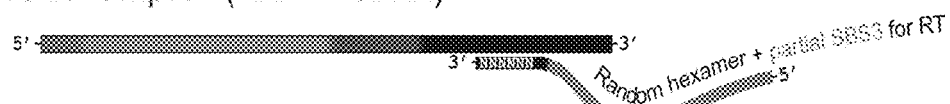
3. Library PCR
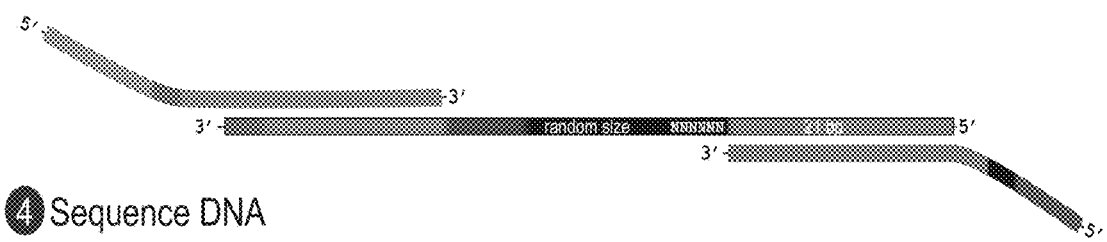
4. Sequence DNA
FIG. 3

Run Summary Exp30-1

| Level | Yield Total (G) | Projected Total Yield (G) | Yield Perfect (G) | Yield <=3 errors (G) | Aligned (%) | % Perfect [Num Cycles] | % <=3 errors [Num Cycles] | Error Rate (%) | Intensity Cycle 1 | % Intensity Cycle 20 | % >= Q30 |
|---|---|---|---|---|---|---|---|---|---|---|---|
| | 10.0 | 10.0 | 0.2 | 0.3 | 2.23 | 51.1 [40] | 96.8 [40] | 1.23 | 3574 | 103.1 | 96.3 |
| | 1.9 | 1.9 | 0.0 | 0.0 | 0.00 | 0.0 [0] | 0.0 [0] | 0.00 | 704 | 0.0 | 94.6 |
| | 5.1 | 5.1 | 0.5 | 0.3 | 3.58 | 77.7 [35] | 96.5 [35] | 1.04 | 2141 | 148.5 | 81.4 |
| | 20.0 | 20.0 | 0.4 | 0.7 | 3.80 | 65.5 | 98.3 | 1.13 | 2128 | 128.3 | 94.2 |

Run Summary Exp002

| Level | Yield Total (G) | Projected Total Yield (G) | Yield Perfect (G) | Yield <=3 errors (G) | Aligned (%) | % Perfect [Num Cycles] | % <=3 errors [Num Cycles] | Error Rate (%) | Intensity Cycle 1 | % Intensity Cycle 20 | % >= Q30 |
|---|---|---|---|---|---|---|---|---|---|---|---|
| | 10.6 | 10.6 | 0.2 | 0.2 | 1.28 | 96.9 [50] | 99.0 [46] | 0.06 | 3170 | 125.7 | 97.9 |
| | 2.4 | 2.4 | 0.0 | 0.0 | 0.00 | 0.0 [0] | 0.0 [0] | 0.00 | 5089 | 0.0 | 98.1 |
| | 13.0 | 13.0 | 0.2 | 0.2 | 1.79 | 94.5 [40] | 96.6 [40] | 0.20 | 4025 | 71.7 | 98.7 |
| | 26.1 | 26.1 | 0.4 | 0.4 | 1.26 | 96.7 | 99.3 | 0.15 | 4246 | 96.7 | 98.9 |

FIG. 27

Read 1    Exp30-1

| | | | % Clusters PF [passing quality filter] | | Million Reads PF [passing quality filter] | | |
|---|---|---|---|---|---|---|---|
| Lane | Tiles | Density (K/mm2) | Cluster PF (%) | Phas/Prephas (%) | Reads (M) | Reads PF (M) | % >= Q30 |
| | 64 | 873 +/- 49 | 71.84 +/- 11.96 | 0.071 / 0.124 | 160.96 | 115.09 | 86.0 |
| | 64 | 893 +/- 39 | 71.25 +/- 9.78 | 0.074 / 0.128 | 164.66 | 117.13 | 86.0 |

Read 1    Exp002

| Lane | Tiles | Density (K/mm2) | Cluster PF (%) | Phas/Prephas (%) | Reads (M) | Reads PF (M) | % >= Q30 |
|---|---|---|---|---|---|---|---|
| | 64 | 853 +/- 118 | 96.64 +/- 1.97 | 0.221 / 0.140 | 157.31 | 151.81 | 97.9 |
| | 64 | 852 +/- 117 | 96.65 +/- 1.97 | 0.220 / 0.146 | 157.01 | 151.39 | 97.9 |

FIG. 28

| | |
|---|---|
| Seq ID No. 8 | /5SpC3/GAATTTAATACGACTCACTATAGGAGTTCAGACGTGTGCTCTTCCGATCTCAGGTTAC |
| Seq ID No. 9 | /5SpC3/GAATTTAATACGACTCACTATAGGAGTTCAGACGTGTGCTCTTCCGATCTGTAACCTG |
| Seq ID No. 10 | /5SpC3/GAATTTAATACGACTCACTATAGGAGTTCAGACGTGTGCTCTTCCGATCTACTTGGCA |
| Seq ID No. 11 | /5SpC3/GAATTTAATACGACTCACTATAGGAGTTCAGACGTGTGCTCTTCCGATCTTGCCAAGT |

FIG. 29

NUCLEIC ACID CONSTRUCTS AND METHODS FOR LABELING AND DETECTING NUCLEOSOMAL DNA MODIFICATIONS

CROSS REFERENCE TO RELATED APPLICATIONS

This application claims the benefit of U.S. Provisional Application No. 62/342,439, filed May 27, 2016, which is incorporated herein by reference in its entirety.

TECHNICAL FIELD

The subject matter disclosed herein is generally directed to methods for detecting nucleosomal DNA modifications. Specifically, the subject matter is directed to labeling of fragmented nucleosomal DNA with adapters that preserve the origin of the fragmented nucleosomal DNA thereby enabling subsequent multiplexed analysis of nucleosomal modifications and the ability to map those modifications back to the cell or cell population from which they originated.

BACKGROUND

Chromatin immunoprecipitation and sequencing (ChIP-seq) can be used to map histone modifications genome-wide, enabling the identification of cell-type-specific functional genomic elements and epigenetic states. However, this technology has several limitations. Recent adaptations of the method can address individual limitations, but there are tradeoffs and limitations to each of these approaches.

First, conventional ChIP-seq procedures involve separate immunoprecipitations (IPs) that are sensitive to the amount of chromatin input and the quality of the antibody. This compromises the accuracy with which chromatin landscapes can be quantitatively compared across samples. The lack of quantitative information in ChIP-seq data is a long-standing problem and can obscure global differences in histone modification levels due to cell state transitions or genetic mutations in epigenetic regulators frequently observed in cancer (Ryan and Bernstein, 2012). Recent studies have presented strategies for quantitatively comparing ChIP-seq signal intensities by incorporating exogenous DNA or synthetic histone spike-in controls, but these protocols may not be compatible with low cell numbers and/or aneuploidy (Bonhoure et al., 2014; Grzybowski et al., 2015; Orlando et al., 2014). Quantitative consistency might also be achieved by combining samples in the same reaction; therefore developing a method for processing many samples in the same ChIP-seq assay would be valuable.

Second, conventional ChIP-seq experiments require large numbers of cells. Progress has been made toward reducing cell requirements, but the corresponding methods do not address the challenge of quantitative comparison, are low throughput, and/or have only been demonstrated for certain modifications (Adli et al., 2010; Brind'Amour et al., 2015; Gilfillan et al., 2012; Lara-Astiaso et al., 2014). Limitations have been addressed by (1) minimizing loss and (2) performing linear amplification of input material, which have individually been demonstrated to increase sensitivity of ChIP experiments (O'Neill et al., 2006; Shankaranarayanan et al., 2011).

Third, the throughput of ChIP-seq is constrained by individual sample processing. Progress has been made toward high-throughput ChIP, but these methods have other limitations such as high input requirements (Chabbert et al., 2015; Garber et al., 2012). Accordingly, what is also needed are methods that increase sample processing throughput.

SUMMARY

In one aspect, the subject matter disclosed herein is directed to methods of labeling nucleosomal DNA. The method may comprise providing one or more individual discrete volumes, each individual discrete volume comprising a cell or population of cells. The cell or cell population is lysed in the individual discrete volume and the nucleosomal DNA fragmented. The fragmented DNA is then modified on at least one free end of the fragmented nucleosomal DNA by ligation of an adapter. The adapter may comprise an amplification promoter, at least a partial sequencing primer binding site, and a barcode. The barcode is a nucleotide sequence unique to a given individual discrete volume and thus preserves the origin of each labeled nucleosomal DNA. The partial sequencing primer binding site may be a first read or second read sequencing primer binding site. The labeled nucleosomal DNA may then be isolated, sequenced, and grouped by common barcode to identify all sequences originating from the same individual discrete volume.

The method may further comprise amplifying the isolated and labeled nucleosomal DNA prior to sequencing. Amplification of the labeled nucleosomal DNA may comprise generating RNA copies of the labeled nucleosomal DNA via in vitro transcription from the amplification promoter of the barcoded adapter. Then, cDNA copies may be generated from the RNA copies using a reverse transcription primer. The reverse transcription primer may comprise a randomized nucleotide portion for binding to the nucleosomal DNA portion of the cDNA and at least a portion of a partial second sequencing primer binding site. If the adapter comprises a partial first read sequencing primer binding site, then the reverse transcription primer comprises a partial second read sequencing primer binding site. If the adapter comprises a partial second read sequencing primer binding site, then the reverse transcription primer comprises a partial first read sequencing primer binding site. The cDNA copies are then amplified using a pair of PCR primers to generate double stranded DNA for sequencing. The PCR primer pair comprises between the forward and reverser primer a complete first read and second read sequencing primer binding sites. The forward and reverse PCR primers bind to the cDNA via the sequencing primer binding sites and corresponding complementary sequences in the cDNA. Thus, the double stranded DNA amplified from the cDNA comprises complete first and second read sequencing primer binding sites.

The above labeling, amplification, and sequencing steps may be further combined with nucleosomal modification assays, such as immunoprecipitation assays, to detect nucleosomal modification in different cells or cell populations. After labeling with the barcoded adapters, all nucleosomal DNA from all samples may be pooled and then split into separate nucleosomal DNA modification detection assays. After conducting the nucleosomal modification detection assay, the labeled nucleosomal DNA may be amplified and sequenced as described above. The sequences may then be grouped according to common barcodes thereby identifying the cell or cell population from which a given nucleosomal modification originated.

In another aspect, the subject matter disclosed herein is directed to the barcoded adapters described above.

In yet another aspect, the subject matter disclosed herein is directed to kits comprising the adapters, reverse transcription primers, and amplification primers described herein. In certain example embodiments, the kits may further comprise reagents needed to carry out the nucleosomal modification detection assays described herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 1 is a schematic showing the process flow for fragmenting and labeling nucleosomal DNA prior to conducting a nucleosomal modification detection assay, in accordance with certain example embodiments.

FIG. 2 is a schematic showing an adapter configuration and amplification and sequencing process flow, in accordance with certain example embodiments.

FIG. 3 is a schematic showing an alternative adapter configuration and amplification and sequencing process flow, in accordance with certain example embodiments.

FIG. 27 provides a set of tables showing sequencing data quality generated using a standard (top) and inverted (bottom) adapter.

FIG. 28 provides a set of tables showing the percent of clusters passing quality filters using a standard adapter (top) and the inverted adapter (bottom).

FIG. 29 provides a set of four adapters used to identify a single individual discrete volume in accordance with certain example embodiments.

DETAILED DESCRIPTION OF THE EXAMPLE EMBODIMENTS

General Definitions

Figure 4:
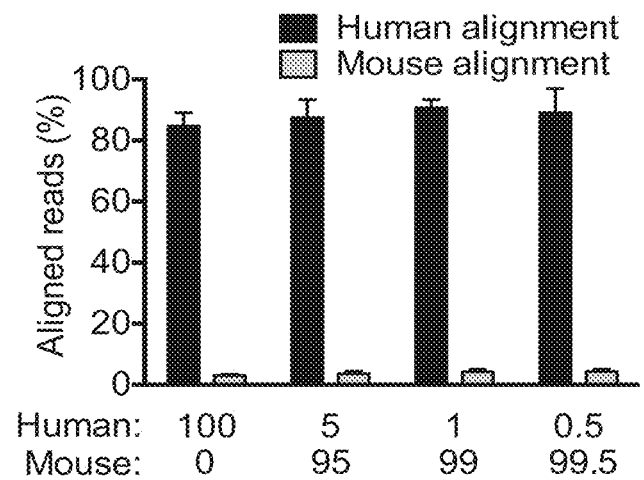
FIG. 4 is a graph showing the portion of sequencing reads generated in accordance with certain example embodiments that align to human or mouse genomes.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application may be considered indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods for identifying cell-type-specific nucleosomal DNA modifications. The methods leverage nucleosomal DNA barcoding and pool-and-split multiplexing to provide high-throughout, quantitative profiling of nucleosomal DNA states. The methods enable the profiling of multiple nucleosomal DNA marks across different cell types and/or conditions thereby linking quantitative changes in chromatin landscapes to different genotypes and chemical and physical perturbations.

A cell or cell population is cultured in one or more discrete volumes. The cell or cell population in each discrete volume is lysed and the nucleosomal DNA fragmented. At least one free end of the fragmented DNA is then labeled via ligation to a barcoded adapter. The barcoded adapter facilitates further amplification and sequencing of the fragmented DNA. The barcode in turn is unique to each individual discrete volume, thereby preserving the origin of the fragmented DNA. All fragmented DNA from all individual discrete volumes may then be pooled and subsequently split into separate nucleosomal DNA modification detection assay sample volumes. A separate nucleosomal modification detection assay may then be conducted on each assay sample volume. The labeled nucleosomal DNA may then be isolated from each assay sample volume. The isolated nucleosomal DNA is then sequenced and grouped according to common barcodes. In this way, nucleosomal modifications may be mapped back to a particular cell or cell population in a given individual discrete volume. In certain example embodiments, the labeled and fragmented nucleosomal DNA may first be amplified prior to isolation and sequencing as described in further detail below.

Initial Assay Set-Up and Individual Discrete Volumes

The methods disclosed herein provide high-throughput methods for assaying genome wide nucleosomal DNA modification states across a wide range of sample types. The samples may comprise a single cell or a population of cells. Likewise, the assays may be used to assess a single cell type or a sample comprising multiple cell types. The cells may be derived from cells cultured in vitro or from cells derived directly from a biological sample, such as a biological sample from a subject to be tested. The cells or cell population may be exposed to different genetic, chemical and physical perturbations to assess the impact such perturbations may have on nucleosomal DNA modifications. Example genetic perturbations include gene knock-ins, gene knock-outs, inversions, translocations, or one or more nucleotide insertions, deletions, or substitutions. Example chemical perturbations include, but are not limited to, exposure to different types and/or concentrations of chemical agents, including therapeutic agents, tool compounds, and drug-like molecules. Example physical perturbations include, but are not limited to, exposure to different temperatures, atmospheric pressures, atmospheric CO2 concentrations, atmospheric O2 concentrations, or changes in pH.

As used herein an "individual discrete volume" refers to a container, a receptacle, or other defined volume or space. The volume or space can be defined by properties that prevent or inhibit migration of target molecules or cells, for example, a volume or space defined by physical properties such as the wall of a well, tube, or surface of a droplet, which may be impermeable or semipermeable. In certain example embodiments, the discrete volumes are suitable for the culturing of live cells. In certain example embodiments, the discrete volume may be the wells of a standard microwell plate, such as a 6 well, 24 well, 96 well, 384 well, or 1,536 well plate. In certain example embodiments, the discrete volume may be a droplet generated on a microfluidic device. In certain example embodiments, the cells are Poisson loaded into droplets such that a single cell is loaded in each droplet.

Lysis and Fragmentation of Nucleosomal DNA

The cell or cell population in each individual discrete volume may be lysed using standard cell lysis techniques known in the art. The cells may be fixed or unfixed prior to lysis.

The nucleosomal DNA is then fragmented. The nucleosomal DNA may be fragmented using methods known in the art. In certain example embodiments, the nucleosomal DNA may be cross-linked prior to fragmentation of the nucleosomal DNA. Thus, in certain example embodiments, the nucleosomal DNA may be cross-linked to proteins binding to the nucleosomal DNA. In certain example embodiments, the nucleosomal DNA may be fragmented enzymatically. For example, the nucleosomal DNA may be fragmented by a DNase, a MNase, a dsDNA fragmentase, a transposase or any other enzyme recognized in the art as suitable for fragmenting nucleosomal DNA. In certain example embodiments, the nucleosomal DNA is fragmented using a MNase. In certain other example embodiments, the nucleosomal DNA may be fragmented using physical means such as, but not limited to, acoustic shearing, sonication, and hydrodynamic shearing. In certain example embodiments, the nucleosomal DNA is fragmented using sonication. For enzymatic fragmentation, an enzyme deactivation step may be applied to the samples. For example, the enzyme may deactivated by addition of a chelator such as EGTA at a concentration and time sufficient to deactivate the enzyme.

Labeling of Nucleosomal DNA with Adapters

After fragmentation, the nucleosomal DNA is labeled with barcoded adapters. In certain example embodiments, an arresting agent is added to arrest chromatin fragmentation activity prior to labeling the fragmented nucleosomal DNA with the adapters. The arresting agent will depend on the enzyme used to fragment the DNA. For example, if micrococcal nuclease (MNase) is used to achieve chromatin fragmentation, EGTA may be added to the nucleosomal DNA preparation to arrest the activity of MNase. The concentration of soluble nucleosomal DNA may then optionally be measured using, for example, a Thermo-Fisher Scientific DNA Qubit assay, prior to commencing the end-repair and adaptor ligation step. The fragmented nucleosomal DNA may labeled with an adapter at one end or both ends of the fragmented DNA. In certain example embodiments, the fragmented nucleosomal DNA ends are end repaired prior to being labeled with the barcoded adapters. Methods for end repair of digested or fragmented DNA ends are known in the art. The adapters are then ligated to one or more free ends of the ligated nucleosomal DNA using standard nucleic acid ligation methods known in the art. In certain example embodiments, the nucleosomal DNA is labeled on only a single free end.

The barcoded adapters may comprise DNA, RNA, nucleotide analogs or a combination thereof. The adapters may be single-stranded or double-stranded. In one exemplary embodiment, the adapters are double-stranded. In one example embodiment, the barcoded adapter comprises an amplification promoter, at least a partial sequencing primer binding site and a barcode sequence. In certain example embodiments, the adapter may further comprise a 5' single stranded spacer to prevent self-ligation and concatemerization of the adapter. The spacer may be any suitable spacer for that purpose. In certain example embodiments the spacer is a carbon spacer, such as a three carbon spacer.

In certain example embodiments, the adapter may comprise one or more modifications that increase adapter stability and/or resistance to degradation. In certain example embodiments, the modifications may be made to one or more terminal bases of the adapter on the 3' end, the 5' end, or both. In one example embodiments, the one or more modifications may be made to the first, second, third, and/or fourth terminal bases of the adapter on the 3' or 5' end of the sense or antisense strand. In certain example embodiments, the one or more modifications are made to the backbone linkages between the first and second terminal bases; the first, second, and third terminal bases; the first, second, third, and fourth terminal bases; or the first, second, third, fourth, and fifth terminal bases of the adapter on the 3' or 5' end of the sense or antisense strand of the adapter. In certain example embodiments, the one or more modifications comprise phosphorothioate linkages between the terminal bases on the 3' or 5' end of the sense or antisense strand. In one example embodiment, the one or more modifications comprise phosphorothioate linkages between the first and second terminal bases; the first, second, and third terminal bases; the first, second, third, and fourth terminal bases; or the first, second, third, fourth, and fifth terminal bases of the adapter on the 3' or 5' end of the sense or antisense strand. In one example embodiment, the one or more modifications comprise phosphorothioate linkages between the first and second terminal bases; the first, second, and third terminal bases; the first, second, third, and fourth terminal bases; or the first, second, third, fourth, and fifth terminal bases of the adapter on the 3' end of the sense strand. In certain example embodiments, the modifications described in the immediately proceeding sentence are further combined with phosphorothioate linkages between the first and second terminal bases; the first, second, and third terminal bases; the first, second, third, and fourth terminal bases; or the first, second, third, fourth, and fifth terminal bases of the adapter on the 5' end of the antisense strand.

In certain example embodiments, the amplification promoter is a RNA polymerase promoter. In certain example embodiments, the RNA polymerase promoter is a viral RNA polymerase promoter. In certain other example embodiments, the RNA polymerase promoter is a T7 RNA polymerase promoter. The classic T7 promoter sequence has a string of three guanosines at the 3' end. This string of three guanosines may result in a non-annealing region between later PCR primers used to amplify a downstream cDNA product as described further below. Thus, in certain example embodiments, the classic T7 promoter may be modified to replace the triple guanosine with other nucleotide sequences that allow for perfect annealing between the 3' end of the cDNA and the PCR primers while retaining proper T7 promoter function.

The amplification promoter is located proximate to at least the partial sequencing primer binding site. As used herein, "sequencing primer binding site" refers to a region comprising a nucleotide sequence complementary to a nucleotide sequence of a sequencing primer and to which the sequencing primer can hybridize to initiate a sequencing read. Thus, the nucleotide sequence of the sequencing primer used will dictate the sequence of the partial sequencing primer binding site on the adapter. In certain example embodiments, a spacer of 1 to 8 nucleotides in length may be located between the amplification promoter and the partial sequencing primer binding site. In certain other example embodiments, the amplification promoter and the partial sequencing primer binding site are directly adjacent to one another. In certain example embodiments, the partial sequencing primer binding site comprises 10, 11, 12, 13, 14, 15, 16, 17, 18, 19, 20, 21, 22, 23, 24 or 25 nucleotides complementary to a sequencing primer. In certain example embodiments, the partial sequencing primer binding site is a first read sequencing primer binding site. In certain example embodiments, the first read sequencing primer binding site is a SBS3 primer binding site. In certain other example embodiments, the sequencing primer binding site is a second read sequencing primer binding site. In certain example embodiments, the second read sequencing primer binding site is a SBS12 sequencing primer binding site. The SBS3 and SBS12 sequencing primers are provided as example only and binding sites based on other suitable sequencing primers may be used.

The partial sequencing primer binding site is proximate to a barcode sequence. In certain example embodiments, a spacer of 1 to 20 nucleotides in length may be located between the sequencing primer binding site and the barcode. In certain example embodiments, the spacer may function as a unique molecular identifier (UMI). The UMI enables further differentiation between any two distinct adapter ligation events that may occur at the same fragmentation site in the nucleosomal DNA from two different cells. In other example embodiments, the first portion of the second read sequencing primer binding site may be located directly adjacent to the barcode sequence. The barcode is a short sequence of nucleotides (e.g. DNA, RNA, or nucleotide analog), for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. In certain example embodiments, the barcode is eight nucleotides in length. The barcode may be used to indicate the individual discrete volume or sample from which isolated and labeled nucleosomal DNAs originated. Thus, a given set of adapters used to label nucleosomal DNAs in a given individual discrete volume may have the same unique barcode. As used herein, such barcodes may be referred to as origin specific barcodes. Likewise, as described further below, a second barcode may be incorporated in a later generated amplicon product to indicate the type of nucleosomal modification assay performed on a given assay sample. In that instance, each assay would be assigned a unique barcode and all samples processed using a given assay would incorporate the same barcode. As used herein, such adapters may be referred to as assay barcodes.

In certain example embodiments, the adapters used to identify a single discrete volume may comprise a set of barcodes, with each set of barcodes identifying a single individual discrete volume. The set may comprise adapters with four, three, or two different barcodes. The barcode of each individual barcode in a given set is unique, and each set of barcodes is unique to an individual discrete volume. For example, all barcodes in first adapter set are used to identify a first discrete volume, all barcodes in a second adapter set are used to identify a second discrete volume, and so on. In certain example embodiments, the adapter set comprises four barcodes. Each barcode in the set is optimized to work together, meaning, each nucleotide is represented at each position of the barcode. See FIG. 29, which shows an example set of barcoded adapters. The underlined portion represents the barcode portion of the adapter. At each position of the barcode, each barcode in the set carries a different nucleotide such that between the four individual barcodes all four nucleotides are represented at each position. In certain sequencing technologies it is important to avoid cycles that are devoid of G and T and that are devoid of C and A for reasons generally related to the spectral qualities of the nucleoside analogs and lasers used. Thus, the above barcode set design avoids this issue. Example adapter sequences are provided in SEQ ID NOs: 1-12, with SEQ ID NOs: 8-11 providing an example adapter set as described in this paragraph.

Nucleosomal Modification Assays

After labeling of adapters, all samples from all individual discrete volumes may be pooled and then split into separate assay volumes. When the individual samples are pooled, an optional normalization step may be employed. A normalization step may be helpful in order to achieve approximate parity in the eventual yield of DNA sequence data from each of the nucleosomal DNA components which are to be pooled together. Different normalization methods known in the art may be used. In one example embodiment, the aforementioned DNA Qubit measurement may be used to achieve normalization of the representation of each component in the pool. In certain embodiments, the pooled sample can be split into separate assays to detect different nucleosomal DNA modifications, such as different chemical modifications of histones or transcription factors. The methods may be used with any assay for detecting modifications to the nucleosomal DNA and/or for detecting proteins bound to the nucleosomal DNA. In certain example embodiments, the nucleosomal DNA modification detection assay detects methylation, phosphorylation, acetylation, ubiquitylation, or sumoylation modifications of nucleosomal DNA and/or proteins bound to the nucleosomal DNA. In certain example embodiments, the assay is used to detect transcription factors, chromatin modifying enzyme complexes and components thereof, chromatin remodeling enzyme complexes and components thereof, modifications to histones, and/or non-canonical histone protein variants. The nucleosomal DNA modification assay may be used to detect the presence or modification of Ago1, Ago2, Ago3, Ago4, AIB1, IKZF3, androgen receptor, dimethyl-arginine, ASH2L, BMI-1, CTCFL, BRD3, BRD4, BRD8, BRD9, Cas9, CDK8, CTCF, DNMT1, DNMT3A, DNMT3B, EED, EKLF, EZH2, FOXG1, FOXP1, GATA-1, histone H3R17me2ak18ac, HDAC1, HDAC5, HDAC5, HDAC6, HI-1, histone H2Av, histone H2A, histone H2B, histone H2BK5ac, histone H2BK12ac, histone H2Bk16ac, H2Bk46ac, histone H2BK120ac, histone H2BK120ub 1, histone H3, histone H3.1, histone H3.2, histone H3ac, H3K4ac, H3K4me1, H3K4me2, H3K4me3, H3R8me2a, H3K9ac, H3K9me1, H3K9me2, H3K9me3, H3S10ph, H3S10phS28ph, H3T11ph, H3K14ac, H3K18ac, H3K23ac, H3K23me2, H3K27ac, H3K27me1, H3K27me2, H3K27me2, H3K27me3, H3K36ac, H3K36me2, H3K36me3, H3K56ac, H3K79ac, H3K79me1, H3K79me2, H4, H4ac, H4R2me2a, H4K5ac, H4K8ac, H4K12ac, H4K16ac, H4K20me1, H4K20me3, HNF-3alpha, HP1alpha, Ikaros, IRF-3, IRF-5, JARID1C, Kat6a, KDM1A, KLF5, LXR-alpha, LXR-beta, Maz, MeCp2, MeCp2, MEIS1, MEIS2, MEIS3, Menin, MITF, MLL, MMSET, MXD1, Nanog, NRF2, NFk H3K36me3, H3K56ac, H3K79ac, H3K79me1, H3K79me2, H4, H4ac, H4R2me2a, H4K5ac, H4K8ac, H4K12ac, H4K16ac, H4K20me1, H4K20me3, HNF-3alpha, HP1alpha, Ikaros, IRF-3, IRF-5, JARID1C, Kat6a, KDM1A, KLF5, LXR-alpha, LXR-beta, Maz, MeCp2, SRF, Supt3h, SUV39H1, Suz12, TCF7L1, Tet1, TRIM28, Trrap, YY1, or a combination thereof. The above modifications are examples only. The methods disclosed herein may be used with any assay suitable for detection of modifications to nucleosomal DNA and/or proteins that bind to nucleosomal DNA. In certain example embodiments, the nucleosomal DNA modification detection assay is an immunoprecipitation assay. In certain example embodiments, the immunoprecipitation assay is a chromatin immunoprecipitation assay (ChIP). The nucleosomal DNA modification detection assay may be carried out using known methods and reagents.

Isolation and Sequencing of Labeled Nucleosomal DNA

After completion of the nucleosomal DNA modification detection assay, the labeled nucleosomal DNA may be isolated and sequenced. In certain example embodiments, the method may be used to label nucleosomal DNA separate from detection of nucleosomal DNA modifications. Regardless, the nucleosomal DNA may be isolated and sequenced directly, or amplified prior to isolation and sequencing. In certain example embodiments, amplification of the labeled nucleosomal DNA comprises first generating RNA copies of the labeled nucleosomal DNA via an in vitro transcription reaction from the adapter amplification promoter. This step generates multiple RNA copies per labeled nucleosomal DNA fragment while maintaining starting species representation and the origin specific barcode previously introduced via adapter ligation.

The resulting RNA is then reversed transcribed into cDNA. In certain example embodiments, the primer used in the reverse transcription assay may comprise a random nucleotide portion and a second partial sequencing primer binding site portion. In certain example embodiments, a spacer of 1 to 8 nucleotides in length may be located between the random nucleotide portion and the partial sequencing primer binding portion. In certain example embodiments, the random nucleotide portion is between 6 and 10 nucleotides in length. In certain example conditions, the random nucleotide portion may be composed of equal or unequal parts of adenine and guanine, thymine and cytosine nucleotides. In certain example embodiments, the random nucleotide portion is a random hexamer. If the barcoded adapter used to label the fragmented nucleosomal DNA above comprises a partial first read sequencing primer binding site, then the reverse transcription primer comprises a partial second read sequencing primer binding site. Alternatively, if the barcoded adapter used to label the fragmented nucleosomal DNA above comprises a partial second read sequencing primer binding site, then the reverse transcription primer comprises a partial first read sequencing primer binding site. In certain example embodiments, if the adapter comprises a partial SBS3 primer binding site, then the reverse transcription primer comprises a partial SBS12 primer binding site (FIG. 2). In certain other example embodiments, if the adapter comprises a partial SBS12 primer binding site, then the reverse transcription primer comprises a partial SBS3 binding site (FIG. 3). Thus, in one example embodiment, the resulting cDNA product comprises, in a 5' to 3' direction, a partial second read sequencing primer binding site, nucleosomal DNA, a barcode, and a partial first read sequencing primer binding site. In other example embodiments, the resulting cDNA product comprises, in a 5' to 3' direction, a partial first read sequencing primer binding site, nucleosomal DNA, a barcode, and a partial second read sequencing primer binding site. An example reverse transcription primer is provided in SEQ ID NO: 26.

The resulting single stranded cDNA or DNA-RNA hybrid may then be amplified using PCR to generate a double stranded DNA amplicon for sequencing purposes. In certain example embodiments, the forward primer may comprise a P7 sequencing adapter, an optional assay barcode to identify the type of nucleosomal DNA modification assay conducted on a given sample volume, and a second read sequencing primer binding site. The barcode may comprise the same or similar structural features of the origin specific barcode discussed previously. The second read sequencing primer binding site may be a SBS12 sequencing primer binding site. The corresponding reverse PCR primer may comprise a P5 adapter sequencing adapter, an optional spacer sequence, and a first read sequencing primer binding site. The spacer may be a 2 to 10 nucleotide spacer. The first read sequencing primer binding site may be a SBS3 sequencing primer binding site. An example forward primer is provided in SEQ ID NO: 13 and example reverse primers are provided in SEQ ID NOs: 14-25.

In certain other example embodiments, the forward primer may comprise a P5 sequencing adapter, an optional spacer sequence, and a first read sequencing primer binding site. The spacer may be a 2 to 10 nucleotide spacer. In certain example embodiments, the first read sequencing primer is a SBS3 sequencing primer binding site. The corresponding reverse PCR primer may comprise a P7 sequencing adapter, an optional assay barcode to identify the type of nucleosomal DNA modification assay conducted on a given sample volume, and a second read sequencing primer binding site. The barcode may comprise the same or similar structural features of the origin specific barcode discussed previously. The second read sequencing primer binding site may be a SBS12 sequencing primer binding site.

The resulting double stranded DNA amplicon preserves the nucleosomal DNA sequence, incorporates sequencing adapters, complete sequencing primer binding sites, an origin specific barcode, and optionally a nucleosomal modification assay specific barcode. The amplified DNA may then be used to generate a sequencing library using known methods in the art. The amplified DNA is sequenced using a suitable sequencing technology, such as a next generation sequencing method. The resulting sequencing data is then demultiplexed based on the one or more barcodes. For example, if an assay specific barcode is incorporated as described above, the sequence data may be demultiplexed based on the assay barcode such that all sequences detected as having a particular nucleosomal DNA modification are grouped first. The sequencing data may then be further grouped according to the origin specific barcode to identify all nucleosomal DNAs having a particular nucleosomal modification and originating from the same cell or cell population and any perturbations that may have been applied to the cell or cell population prior to conducting the assay.

Microfluidic Based Applications

As noted above the, the methods disclosed herein may be carried out in standard reaction tubes, microwell plates, and other suitable reaction containers. However, the methods may also be adapted for use with microfluidic reaction devices. A group of cells or single cells may be encapsulated within a droplet on a microfluidic device using known techniques in the art. The cell-containing droplet may then be merged with a series of droplets comprising reagents necessary to carry out the various steps disclosed herein. For example, the cell-containing droplet may be merged with a second droplet comprising cell lysis reagents followed by merger with a third droplet that comprises a nuclease enzyme, such as those discussed above. Alternatively, and to the extent reaction conditions are compatible, the reagents needed to carry out more than one step may be contained within a single droplet. For example, lysis reagents and fragmentation reagents may be comprised in a single droplet.

In certain other aspects, the invention is directed to the adapters described herein, as well as kits incorporating the adapters and various reverse transcription and PCR primers disclosed herein. The kits may further comprise the reagents necessary to carry out the various enzymatic reactions and nucleosomal DNA modification assays that may be used in conjunction with the methods disclosed herein.

The invention is further described in the following examples, which do not limit the scope of the invention described in the claims.

EXAMPLES

Example 1

First, procedures for simultaneously lysing and digesting chromatin from small numbers of K562 cells were modified. Specifically, micrococcal nuclease (MNase) digestion conditions were identified that yield fragments of one to five nucleosomes, which is optimal for ligation and ChIP (O'Neill et al., 2006). Barcoded adapters were then designed that could be ligated to the DNA ends of the fragmented nucleosomes. These double-stranded adapters contain a T7 promoter, an Illumina SBS3 PCR priming sequence, and a barcode that is unique for each sample (termed index #1). They also contain a 5 prime C3 spacer to prevent self-ligation. The T7-adapters were then ligated to the nucleosomes in each sample.

Next, up to 12 ligated chromatin samples were pooled, each containing a different barcode. Unlabeled carrier chromatin was also added to further improve ChIP efficiency (O'Neill et al., 2006). These pooled contents were then split into different ChIP assays, one for each of the following chromatin epitopes: H3 lysine 4 tri-methylation (H3K4me3), H3 lysine 27 acetyl (H3K27ac), H3 lysine 27 tri-methylation (H3K27me3), and total H3. The ChIP assays were carried out using standard procedures and isolated immunoprecipitated DNA for these modifications in four parallel reactions. The size of input and immunoprecipitated DNA was within expected ranges.

An optimized T7 promoter was used to amplify the ChIP DNA in an in vitro transcription reaction (Tang et al., 2005). This step generates multiple RNA copies per chromatin fragment while maintaining starting species representation (Hoeijmakers et al., 2011; Liu et al., 2003). Only one end of the chromatin fragment needs to be adapter-ligated for amplification, which increases efficiency for low-input samples. In vitro transcription conditions for robust amplification of T7-adapter-ligated nucleosomal DNA were identified, with a typical reaction yielding ~1,350 ng of single-stranded RNA (ss)RNA from ~30 ng of ChIP DNA. Carrier chromatin, which lacks T7-adapters, is not retained in this procedure: addition of a 200-fold excess of mouse carrier chromatin to T7-adapter-ligated human chromatin in the ChIP assay did not lead to a detectable increase in reads aligning to the mouse genome (FIG. 4).

Amplified RNA is then reverse transcribed using primers that contain a random hexamer flanked by an Illumina SBS12 PCR priming sequence. The resulting single-stranded cDNA contains priming sequences on both ends. These priming sequences are used to generate a seq library for each ChIP assay (i.e., each histone modification). A second barcode (index #2) is added during the library construction PCR to identify the ChIP assay. Libraries representing different ChIP assays (index #2) were subsequently combined, each containing different starting samples (index #1 on the original T7-adapter) for a single paired-end sequencing run.

Figure 5:
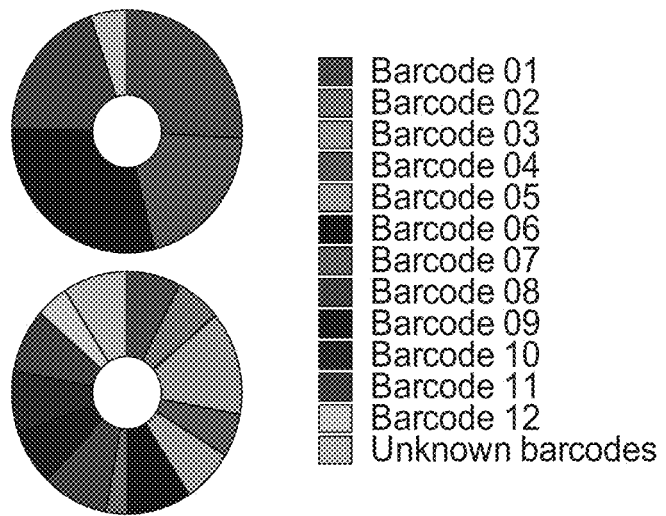
FIG. 5 is a set of pie charts indicating the barcoded adapter representations in sequencing data generated in accordance with certain example embodiments for assessing total H3.
Figure 6:
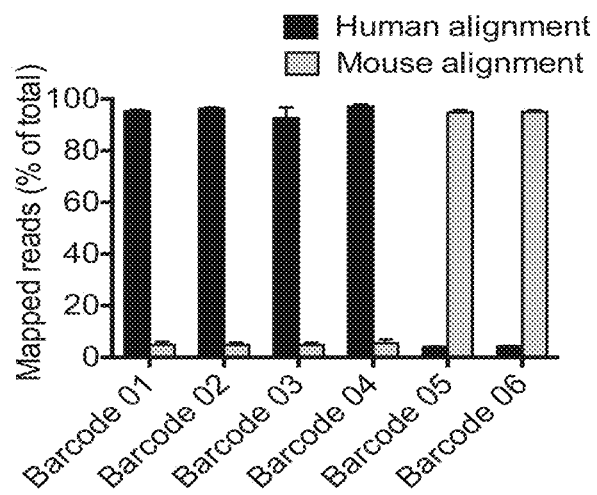
FIG. 6 is a graph showing the results of four human samples (K562, T7-adapter barcodes 1-4) and two mouse samples (YAC-1, T7-adapter barcode 5-6) that were indexed, pooled, and split for three parallel ChIP assays in accordance with certain example embodiments, and depicts the proportions of reads for each barcode that align with human or mouse genomes.

Algorithms were developed to process Mint-ChIP seq results. First, the seq reads are de-multiplexed by index #2 to yield separate read files for each ChIP assay. Each of these read files is then further de-multiplexed by index #1 (T7-adapter barcode) to yield separate files for each sample. All barcodes were represented in the de-multiplexed data, indicating success of the individual ligation reactions. More than 90% of reads were successfully assigned to one of the T7-adapter barcodes (FIG. 5). To check for cross-contamination between barcodes, barcoded chromatin from different species in the same ChIP assay were combined. It was confirmed that 95% of the de-multiplexed reads align specifically to the expected genome sequences (FIG. 6). An additional 4% of reads align to both species, while just 1% of reads align specifically cross species. A stringent procedure to ensure that each nucleosomal fragment is represented by no more than one read was introduced. Any duplicate reads with the same genomic sequence appended to the T7-adapter index were removed, thus alleviating amplification bias.

Figure 7:
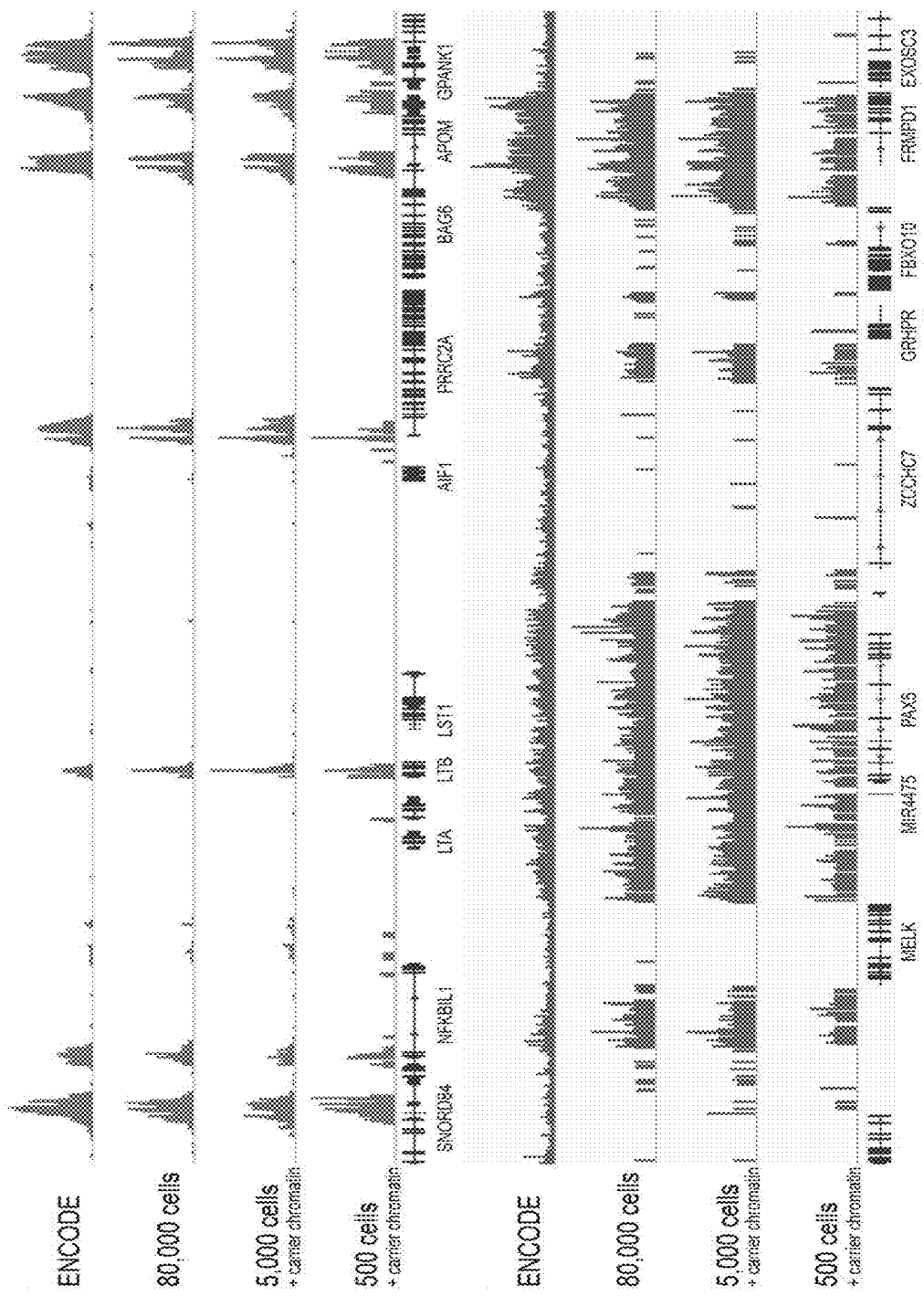
FIG. 7 is a graph showing the H3K4me3 (upper) and H3K27me3 (lower) profiles derived in accordance with certain example embodiments and the starting cell numbers. For comparison, ENCODE data generated by conventional ChIP-seq are also shown.
Figure 8:
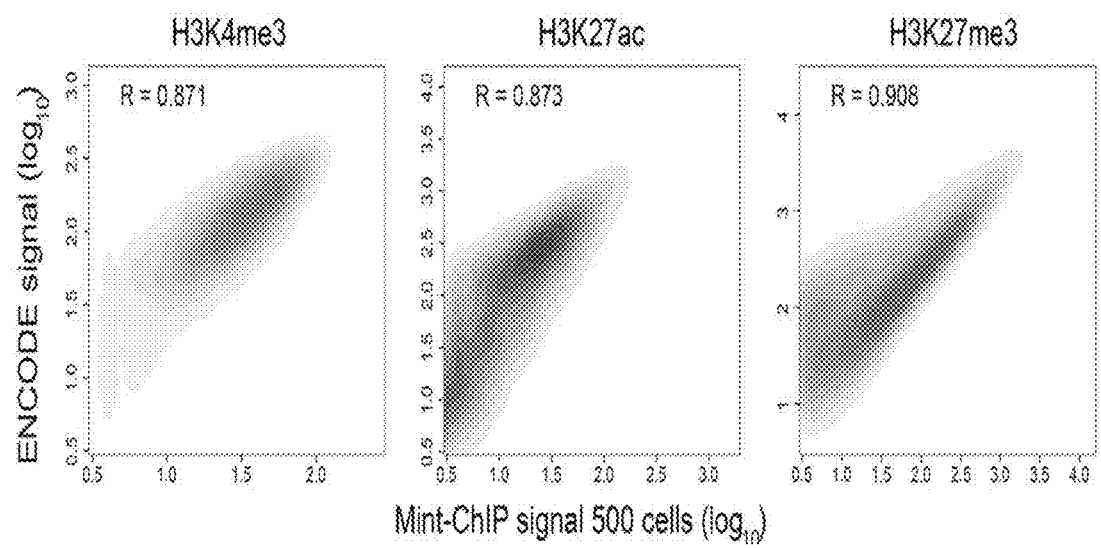
FIG. 8 shows density plots comparing sequencing data generated in accordance with certain example embodiments and ENCODE data for K562 cells. The data points compare the number of reads from the example method (X-axis) versus ENCODE (y-axis) for all promoter intervals (H3K4me3), H3K27ac peaks called from ENCODE data, or all annotated transcripts (H3k27me2). The R indicates Pearson correlation.

The procedure was initially demonstrated using variable numbers of K562 cells and antibodies for H3K4me3, H3K27me3, H3K27ac, and total H3. Barcoded chromatin were prepared from input quantities ranging from 500 to 100,000 cells at different MNase concentrations. The resulting libraries were sequenced and signal tracks visualized for each condition (FIG. 7). Tracks for H3K4me3, H3K27ac, and H3K27me3 revealed expected signals over promoters, distal elements, and Poly-comb-repressed regions, respectively. To evaluate accuracy more precisely, wide comparisons were performed against analogous data generated for the ENCODE project using conventional ChIP-seq technology (Dunham et al., 2012). Comparisons of signal intensities for each mark confirmed high genome-wide correlations between the respective data sets (H3K4me3: R=0.87, H3K27ac: R=0.87, and H3K27me3: R=0.91; FIG. 8). In addition, high correlations were observed between profiles performed using different MNase concentrations and profiles derived from 100,000 and 500 cells. Thus, performing the methods disclosed herein with as few as 500 cells yield accurate and consistent chromatin profiles.

The fraction of successfully aligned reads and the number of unique T7-adapter ligated chromatin fragments at different starting cell numbers was examined. Regardless of input cell number, the percentage of unmapped reads was 6%-14%, indicating that few artifacts were introduced during sample amplification. Working with low input samples can result in IP of a small number of unique chromatin fragments and excessive amplification then leads to a high rate of duplicated reads (Brind'Amour et al., 2015; Gilfillan et al., 2012). Such low complexity libraries contain limited information. The PreSeq package was used to estimate the number of unique nucleosomal fragments immunoprecipitated from different numbers of K562 cells (Daley and Smith, 2013). For 100,000 and 5,000 K562 cells, library complexity was sufficient to generate high-resolution datasets. Using 1,000 and 500 cells resulted in libraries of limited complexity. Still, the chromatin profiles generated from 500 K562 cells were informative and similar to corresponding ENCODE data (FIG. 7-8). Thus, the methods disclosed herein enable analysis of less than 1,000 cells, pushing the boundaries of chromatin profiling.

Figure 9:
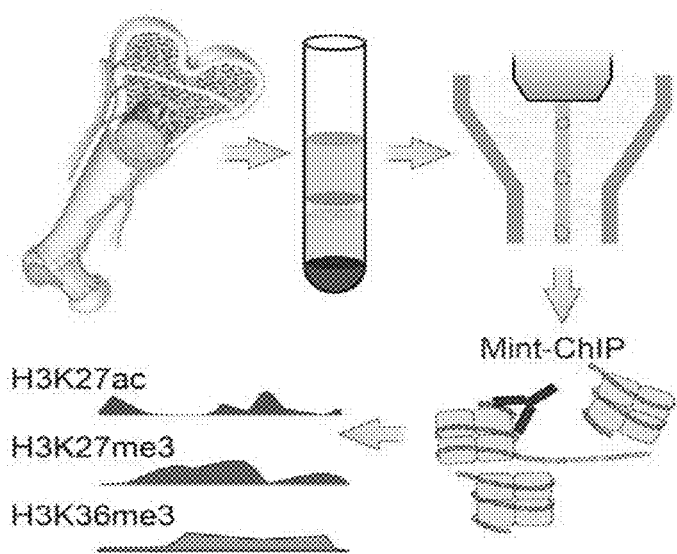
FIG. 9 is a schematic showing an example workflow for hematopoietic stem cell analysis, in accordance with certain example embodiments.
Figure 10:
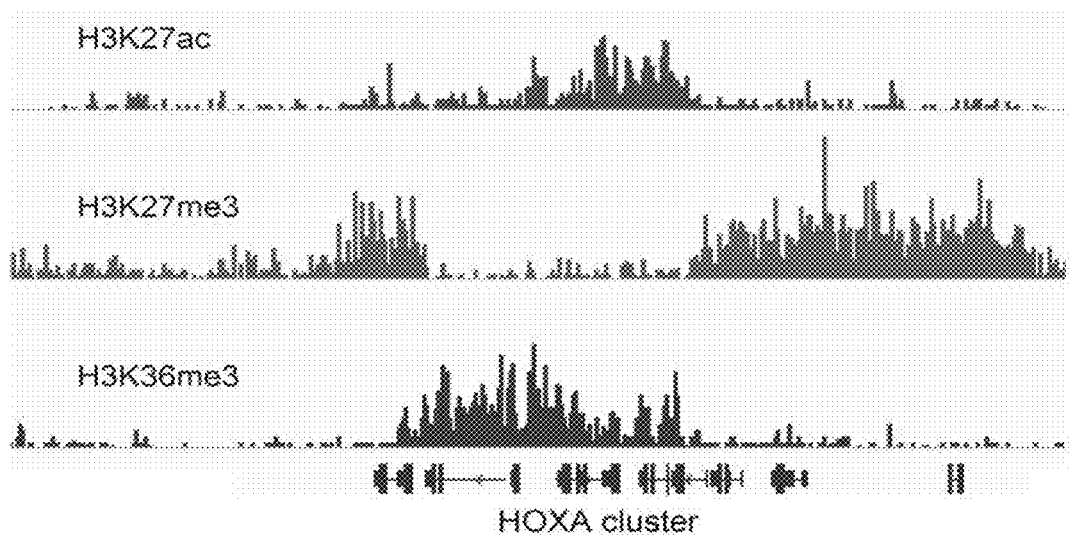
FIG. 10 is a data tracks graph showing H3K27ac, H3K27me3, and H3K36me3 profiles of hematopoietic stem cells at the HOXA locus, generated in accordance with certain example embodiments.
Figure 11:
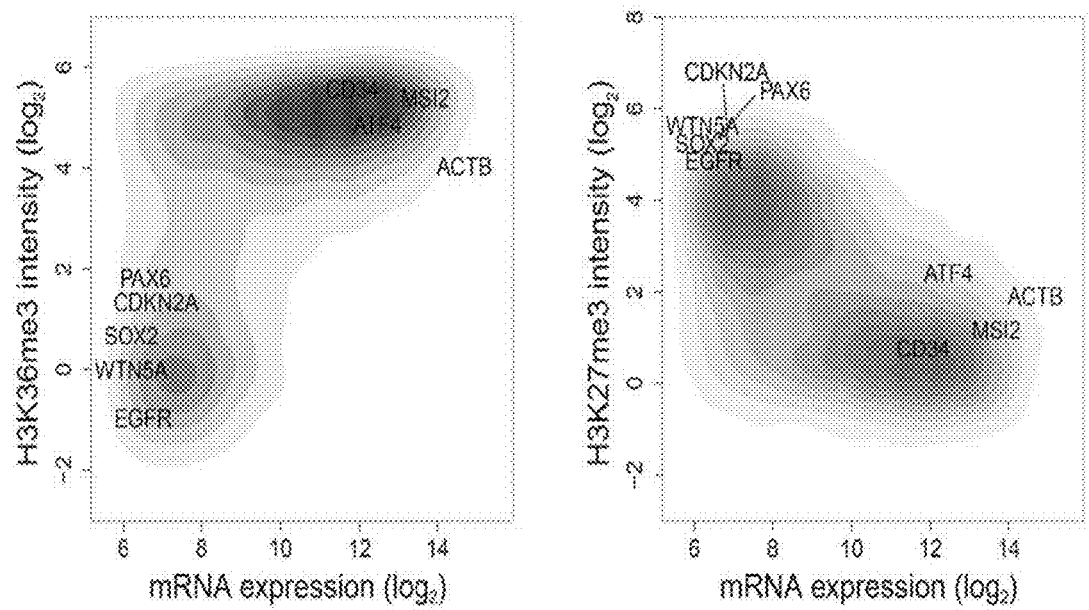
FIG. 11 provides a set of density plots depicting the correlation between methylation with genes (H3K36me3 and H3K27me3) and mRNA expression in human hematopoietic stem cells. Each data point corresponds to a single gene; some genes are highlighted as examples. The data were generated in accordance with certain example embodiments.

To demonstrate the technology on a challenging biological sample, a map of activating and repressive histone modifications in primary human hematopoietic stem cells, which make up less than 0.1% of bone marrow cells, was attempted. CD34+ progenitors were isolated from the bone marrow of an individual and flow sorted CD34+ CD38_CD45RA_cells (FIG. 9). The methods disclosed herein were used to profile H3K27ac, H3K27me3, and H3K36me3 in this population, using 6,000 cells per mark. More than 96% of reads were successfully aligned to the human genome and visual analysis of tracks suggested high-quality data (FIG. 10). Integration with published mRNA expression data showed expected positive (H3K36me3) and negative (H3K27me3) correlations between histone methylation and gene expression (FIG. 11) (Laurenti et al., 2013). For example, CD34 and MSI2 are highly expressed and marked by H3K36me3, whereas SOX2 and PAX6 are repressed by H3K27me3. These data show that the methods disclosed herein can be used to investigate chromatin landscapes of rare primary human cells.

Figure 12:
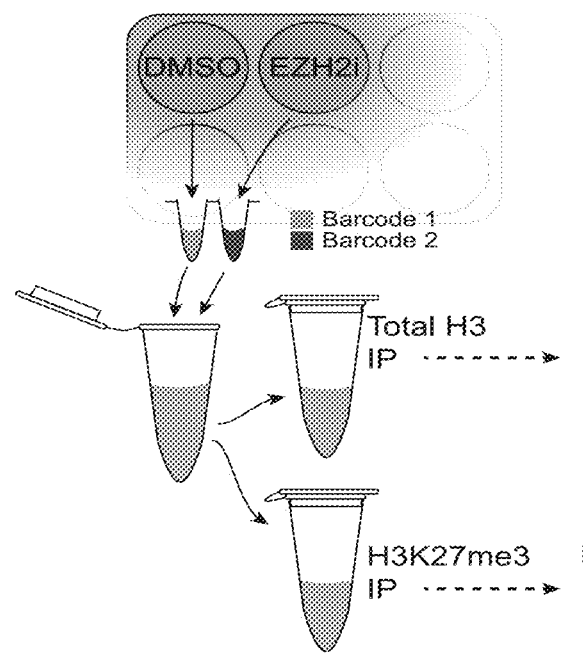
FIG. 12 is a schematic showing an example method for quantitatively normalizing sequencing data results, in accordance with certain example embodiments. The control or drug treated cells are indexed, pooled, and then split for parallel ChIP assays. The ratio between H3K27me3 reads and H3 reads is used to compare global H3K27me3 levels between sample and normalized corresponding profiles.
Figure 13:
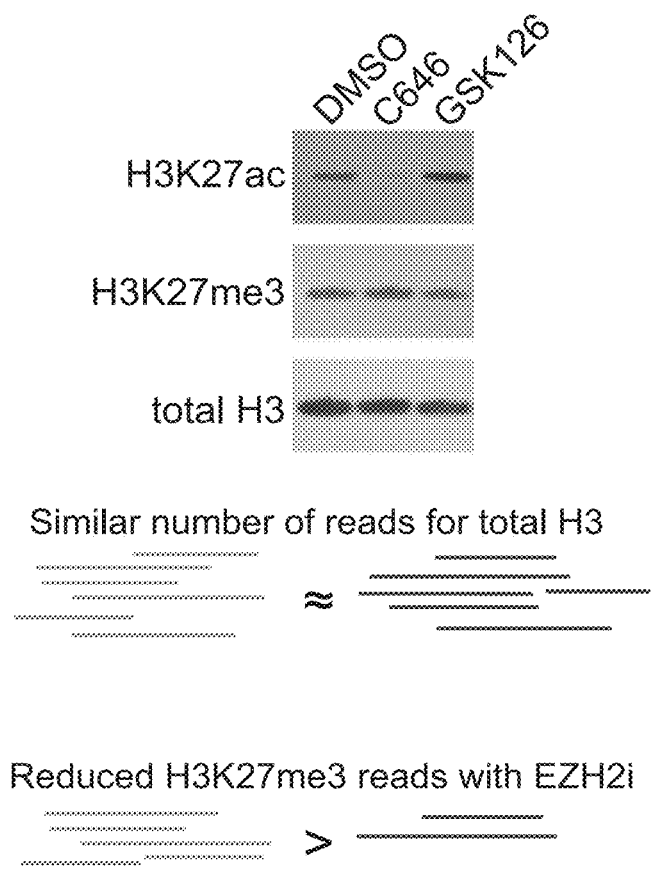
FIG. 13 is a western blot showing H3K27ac and H3K27me3 levels in K562 cells following treatment with the p300 inhibitor C646 or the EZH2 inhibitor GSK125 (compared to a DMSO control). The total H3 is shown as loading control.
Figure 14:
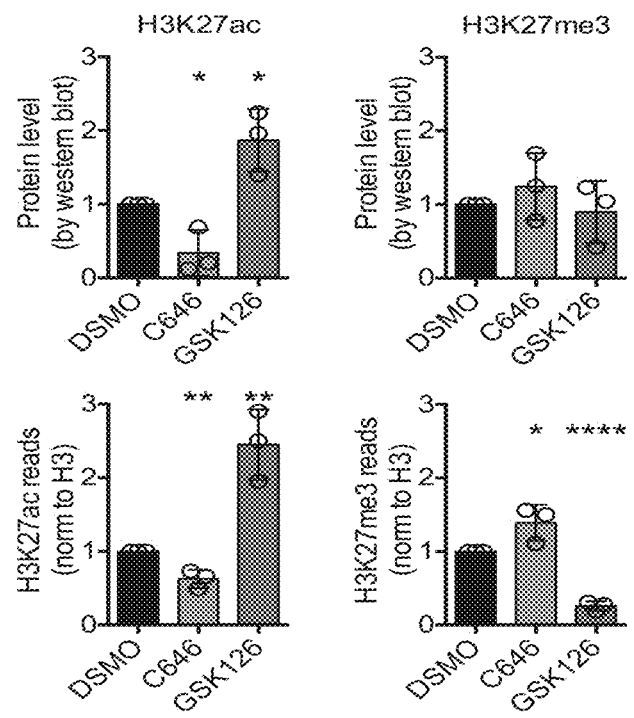
FIG. 14 is a set of bar graphs showing global modification levels inferred from Western blot (top) or in accordance with certain example embodiments (bottom). The respective methods were applied in parallel to the same sample of K652 cells treated for 48 hours with the indicated inhibitors. The data are shown as a mean±SD of n=3 independent experiments (symbols indicate values from independent experiments).

Conventional ChIP-seq does not maintain quantitative information regarding the global abundance of a particular histone modification. Data are typically normalized based on read numbers ("reads per million" or RPM). This presents complications when comparing between samples. To address this shortcoming, exogenous spike-in controls or semisynthetic standards were recently introduced (Bonhoure et al., 2014; Grzybowski et al., 2015; Orlando et al., 2014). The methods disclosed herein were assessed to determine whether the consistency of pooled sample processing could allow the capture of global modification levels without spike-in controls. To this end, an additional IP was included with antibody to total H3, which was used as a normalization factor for the modifications (FIG. 12). The approach for measuring global changes was tested using small molecule inhibitors. K562 cells were treated with the p300 inhibitor C646 or the EZH2 inhibitor GSK126 (Ferrari et al., 2013; McCabe et al., 2012a). Western blots confirmed that H3K27ac levels were reduced by the acetyltransferase inhibitor C646, but increased by the methyltransferase inhibitor GSK126 (FIG. 13). Western blots did not detect significant changes in H3K27me3 levels following 48 hr of either treatment. In parallel, chromatin samples were barcoded from the various treatment and control conditions and these samples were pooled in assays for H3K27ac, H3K27me3, and total H3. After sequencing, the number of reads for H3K27ac and H3K27me3 were normalized to the number of reads for total H3. Consistent with Western blots, p300 inhibitor treatment decreased the ratio between H3K27ac reads and total H3 reads, while the EZH2 inhibitor treatment increased this ratio (FIG. 14). The methods disclosed herein also detected a consistent reduction in H3K27me3 levels following EZH2 inhibitor treatment, which was not evident by Western blot at this early time point.

It is noted the methods disclosed herein are preferential to open regions, as these are more sensitive to MNase digestion. This is evident in the relatively higher proportion of H3 reads that align to euchromatic regions (2-fold enrichment; compare to 1.2-fold enrichment in conventional ChIP-seq). These ratios are small relative to enrichments in ChIP-seq peaks, which range from 5- to 100-fold. However, they could account for increased sensitivity to early changes in H3K27me3 if these were also preferential to euchromatin. To test this, Western blots to quantify H3K27me3 levels were used in MNase digested chromatin from K562 cells treated with GSK126. Consistent reductions in H3K27me3 after 48 hr of treatment were observed, in contrast to conventional Western blots performed on acid extracted histones, which did not reveal a significant change at this early time point. This suggests that nucleosome turnover may lead to a more rapid reduction of methylation levels in euchromatic regions following EZH2 inhibition, in contrast to more stable hetero-chromatic regions. It also suggests the potential of quantitative, multiplexed profiling to detect early changes following epigenetic drug treatment.

Figure 15:
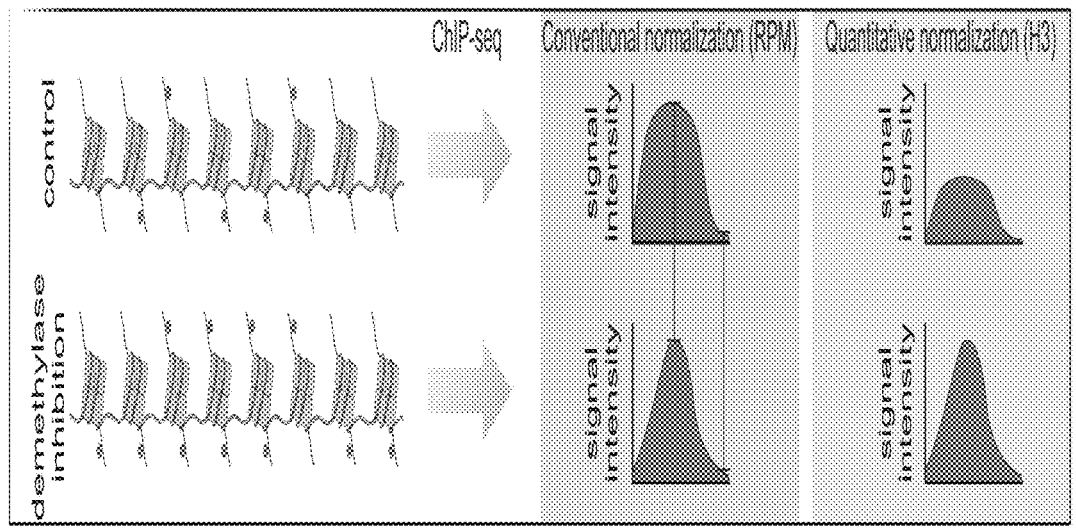
FIG. 15 is a diagram explaining differences between normalization methods. The global differences in histone modifications levels (e.g. by demethylase inhibition) may be masked by conventional ChIP-seq signal normalization (RPM). In contrast, quantitative normalization enables direct peak height comparisons between the samples.
Figure 16:
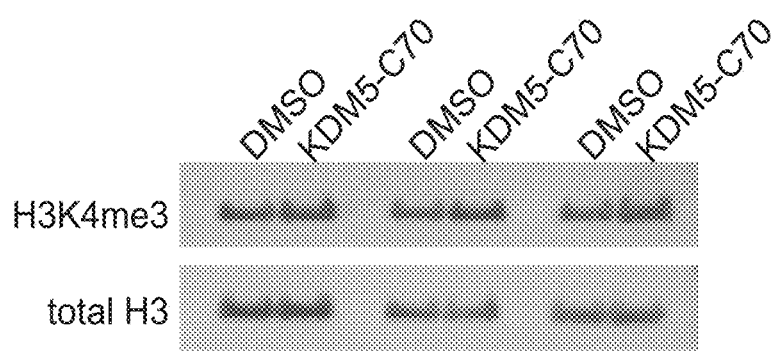
FIG. 16 are Western blots showing increased H3K4me3 levels in K562 cells following treatment with the demethylase inhibitor KDM5-C70. The total H3 is shown as loading control and n=3 experiments are shown.
Figure 17:
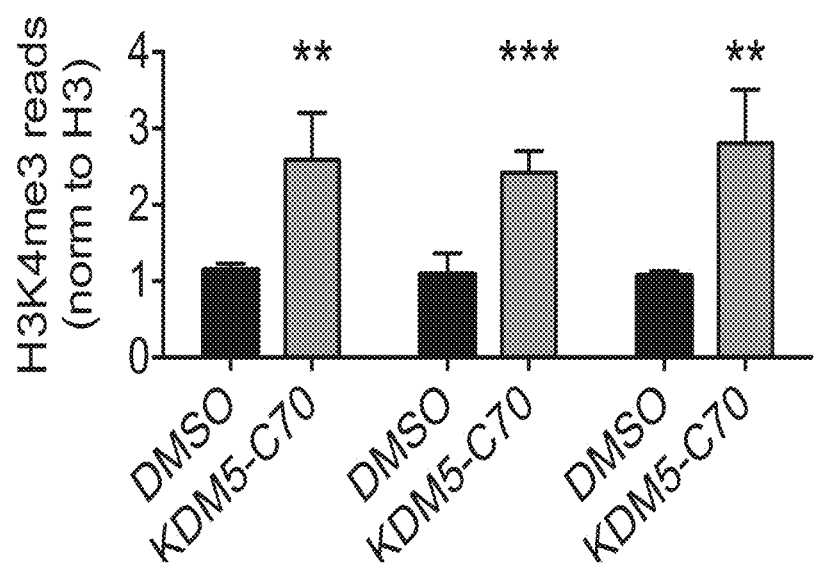
FIG. 17 is a set of graphs showing global H3K4me3 levels inferred in accordance with certain example embodiments. The data are shown as ±SD of four replicates n=3 experiments are shown.
Figure 18:
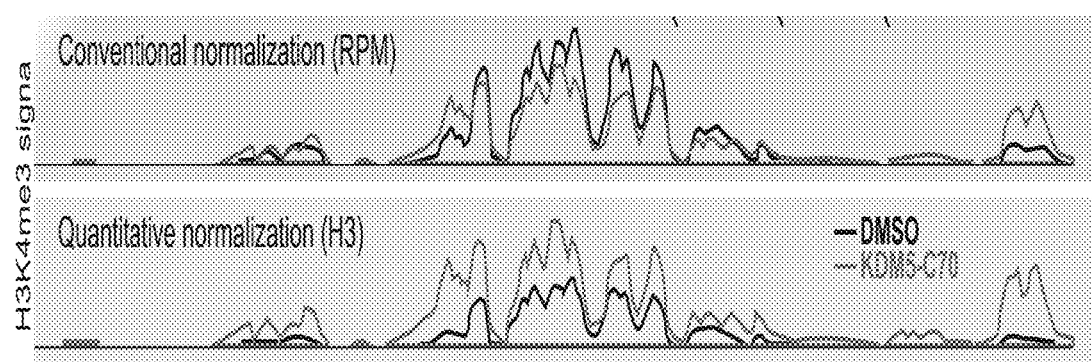
FIG. 18 is a graph showing H3K4me3 profiles scaled by conventional or quantitative normalization.
Figure 19:
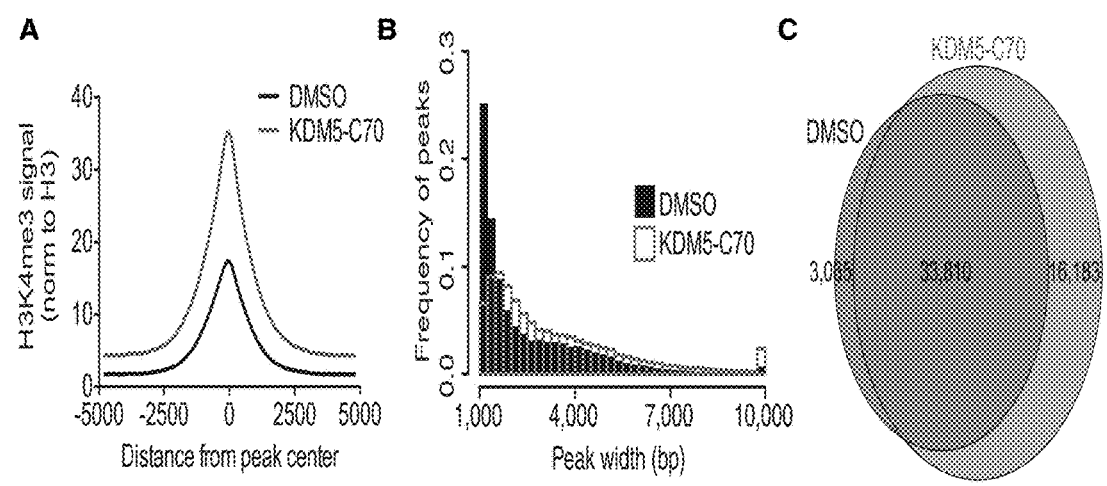
FIG. 19 provides a composite plot depicting average H3K4me3 in K562 cells treated with DMSO or KDM5-C70 (A) with 10 kb regions surrounding the centers of 36,875 peaks that are shown; a bar blot showing the fraction of peaks within size windows (B); and a Venn diagram showing the number of peaks detected in K562 cells treated with DMSO or KDM5-70 (C). The data were generated in accordance with certain example embodiments.

The quantitative accuracy of the methods disclosed herein was further demonstrated by examining the global and locus-specific effects of the H3K4 demethylase inhibitor, KDM5-C70 (FIG. 15). (Labelle et al., 2014). The chromatin of K562 cells treated with DMSO or KDM5-C70 for 96 hr were barcoded and pooled. H3K4me3 and total H3 were then assayed. After sequencing, normalization of the number of H3K4me3 reads to the number of H3 reads reflected global modification levels and was consistent between experiments and also with Western blot analysis (FIG. 16 and FIG. 17). Scaling of the H3K4me3 tracks by the inferred global levels allowed direct comparison of peak height, which clearly showed increased peak intensity following KDM5-C70 treatment. This effect was obscured when the data were subjected to conventional RPM normalization (FIG. 18). Analyses revealed that inhibition of H3K4 demethylases increases H3K4me3 coverage and widens existing domains, while also generating new H3K4me3 peaks (FIG. 19). These data illustrate the utility of the methods disclosed herein for studying chromatin modifiers and epigenetic drugs.

Subunits of the H3K27 methyltransferase Polycomb Repressive Complex 2 (PRC2) are subject to inactivating and gain-of-function mutations in leukemia and lymphoma, respectively (Lund et al., 2013). Two lymphoma cells lines and one leukemia cell line were examined with alternative PRC2 mutations. The lymphoma cell line Pfeiffer has increased PRC2 activity due to the gain-of-function mutation EZH2-A677G (McCabe et al., 2012b). The leukemia line SKM-1 has altered PRC2 activity due to an EZH2-Y641C mutation and an ASXL1 truncation (Ryan et al., 2011; Sneeringer et al., 2010; Wigle et al., 2011). The lymphoma cell line Toledo has no known PRC2 mutations, but was reported to have mutations in the H3K27 acetyl-transferases EP300 and CREBBP (Andersen et al., 2012).

Figure 20:
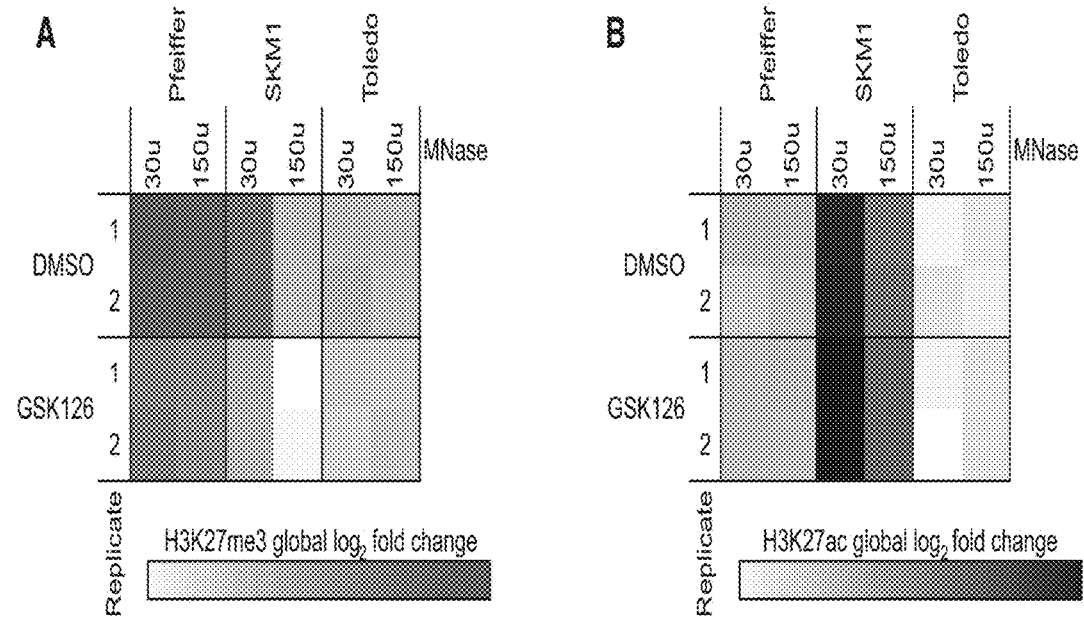
FIG. 20 provides a set of heat maps comparing H3K27me3 (A) and H3K27ac (B) levels in different cell lines treated with GSK126, as quantified in accordance with certain example embodiments. The experiments were performed using two different MNase concentrations.
Figure 21:
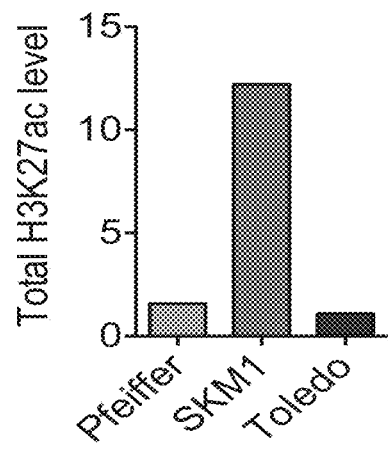
FIG. 21 is bar plot showing mass spectrometry quantification of H3K27ac in Pfeiffer, SKM-1, and Toledo. The mass spectrometry data match the normalized data generated in accordance with certain example embodiments.
Figure 22:
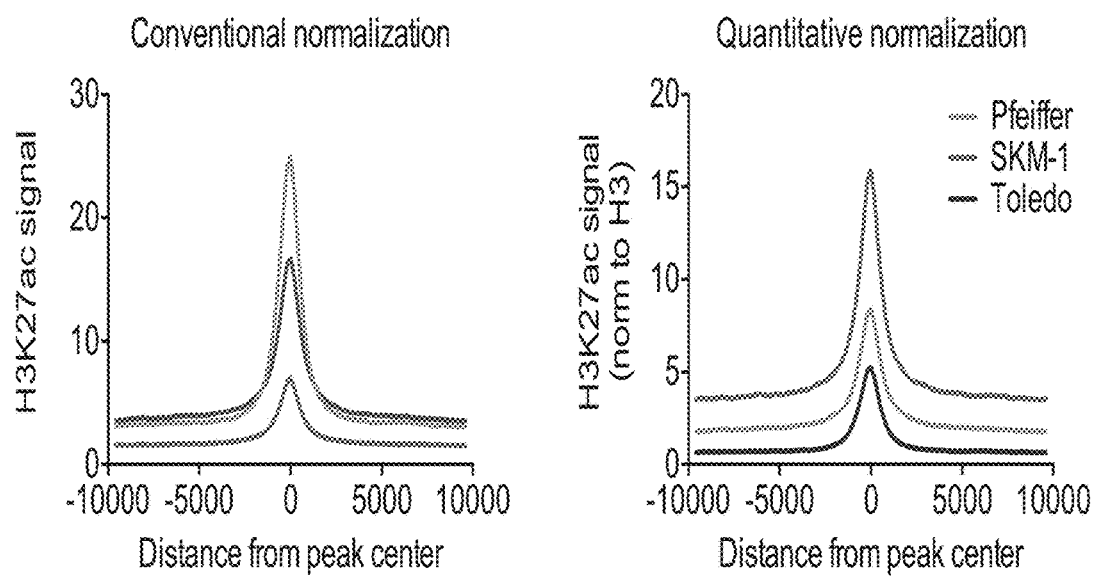
FIG. 22 provides two composite plots depicting average H3K27ac signals over 20 kb regions surrounding the centers of 23,176 peaks. The values were computed by conventional normalization, wherein signal is relative total read numbers (RPM, left) or by the quantitative normalization afforded by example methods disclosed herein (right).

The methods disclosed herein were used to quantitatively compare H3K27me3 and H3K27ac landscapes in these three cell lines. First, the global modification levels based on the ratio of H3K27me3 (or H3K27ac) reads to H3 reads were quantified. H3K27me3 levels were 5.1-fold greater in Pfeiffer than the other cell lines, consistent with its EZH2 activating mutation (FIG. 20). In contrast, the SKM-1 line exhibits 8.7-fold higher global levels of H3K27ac, consistent with mass spectrometry data (FIG. 21) (Jaffe et al., 2013). Notably, the increased H3K27ac in SKM-1 was not restricted to punctate peaks, but rather appears to be diffusely distributed across much of the genome: just 3.4% of H3K27ac reads fall within defined peaks in SKM-1 (compare to 52.4% for Toledo and 42.3% for Pfeiffer). This atypical distribution causes conventional normalization algorithms to show low-intensity H3K27ac peaks in SKM-1, whereas normalization of results achieved using the methods disclosed herein reveals globally increased H3K27ac that was also detected by mass spectrometry (FIG. 22).

Figure 23:
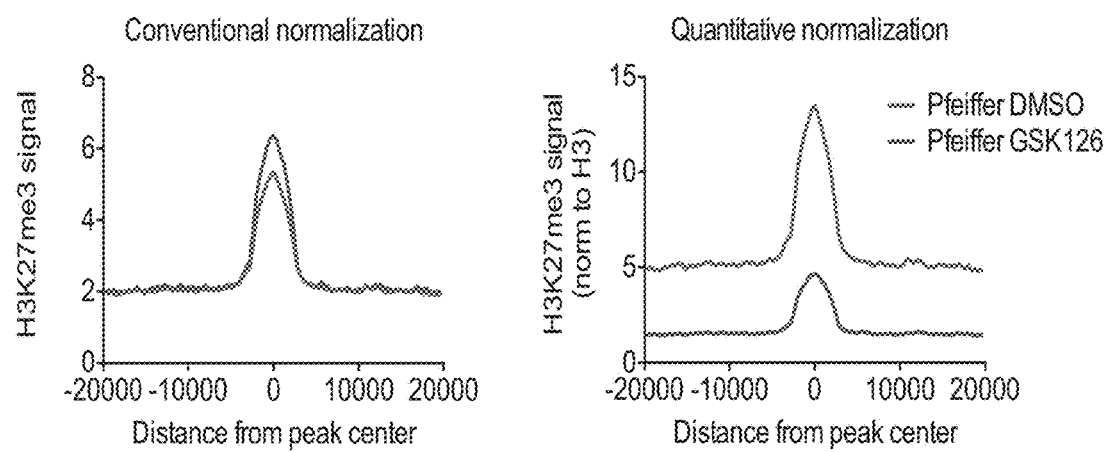
FIG. 23 provides two composite plots depicting average H3K27me3 signals over 40 kb regions surrounding the centers of 2,052 peaks. Together, these data demonstrate the unique capacity of the methods disclosed herein to quantitatively map and compare chromatin landscapes and modification levels between cell types and epigenetic inhibitor treatments.
Figure 24:
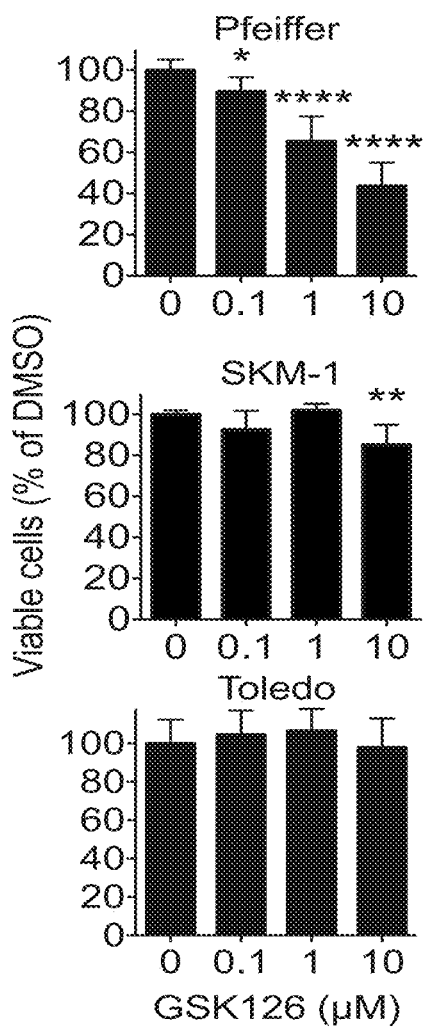
FIG. 24 provides a set of bar plots depicting viable cell counts following 72 hour GSK126 treatment of Pfeiffer, SKM-1, and Toledo. The data are shown as mean±SD of technical triplicates×n=2 independent experiments (*p<0.05, p<0.01, and **p<0.0001).

The respective mutant lines were also treated with the EZH2 inhibitor GSK126, which reduced global H3K27me3 levels (Pfeiffer: 3.4-fold; SKM-1: 3.8-fold; and Toledo: 1.4-fold after 72 hr). Pfeiffer cells, which had the largest absolute decrease in H3K27me3, were the most sensitive to GSK126 treatment (Pfeiffer: 56±11% cell death after 3 days; SKM-1: 15±10%; and Toledo: 2±15%; FIG. 24) (McCabe et al., 2012a). H3K27me3 peaks were called in the naive and drug treated cell lines. Although treatment-associated changes in H3K27me3 are masked by conventional normalization, these changes are readily evident using the quantitative normalization inherent to the methods disclosed herein (FIG. 23). Thus, the methods disclosed herein can quantify differences in global chromatin landscapes of cancer cells representing different genotypes or drug treatments.

Example 2

Figure 25:
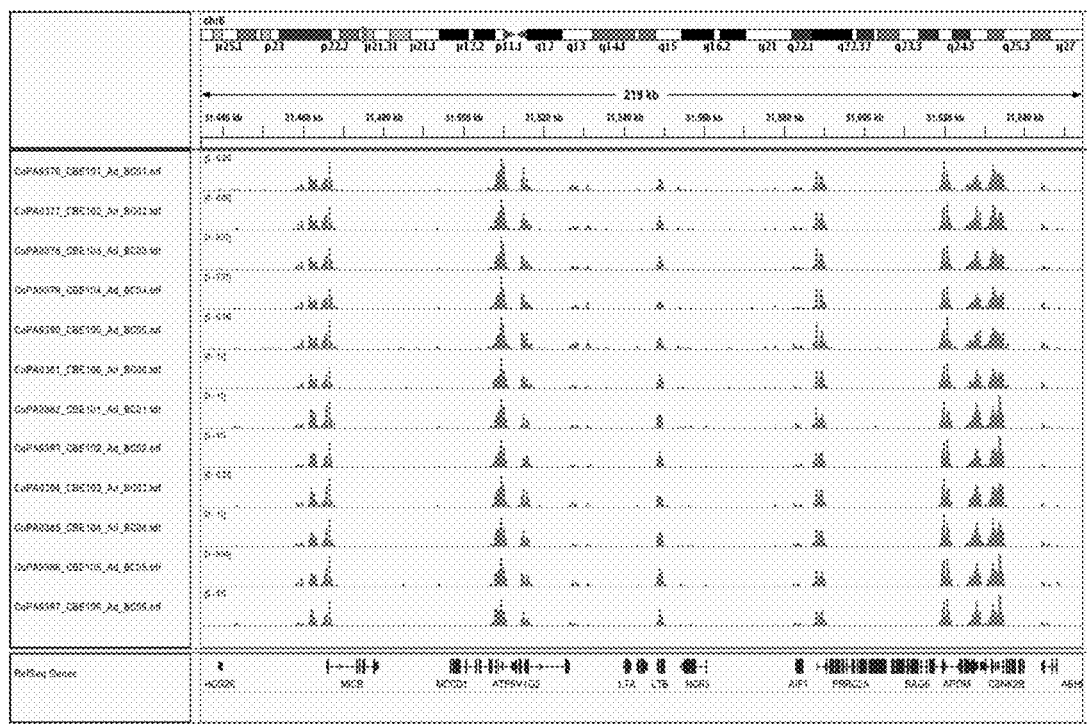
FIG. 25 is a chart showing genome browser tracks derived from sequencing data generated using the inverted adapter configuration illustrated in FIG. 3, and showing the frequency with which DNA is found at each location in the genome.

It was found that inverting the orientation of the first read and second read sequencing primer binding sites on the adapters may increase the quality of the sequencing data in certain circumstance. The following data was generated using the adapter configuration and amplification protocol shown in FIG. 3. Use of the adapter configuration shown in FIG. 3 results in the first read sequencing primer binding site being located adjacent to the variable nucleosomal region. For ease of reference, the configuration shown in FIG. 3 will be referred to hereinafter as the "inverse adapter" and the adapter configuration in FIG. 2 as the "standard adapter." FIG. 25 show the results of operating the inverse adapter configuration in the sequencing process. The graph shows the frequency in which DNA is found at each location in the genome (represented on the X axis). FIG. 25 shows a small region on human chromosome 6 and shows data that would be expected using a standard ChIP-seq assay.

Figure 26:
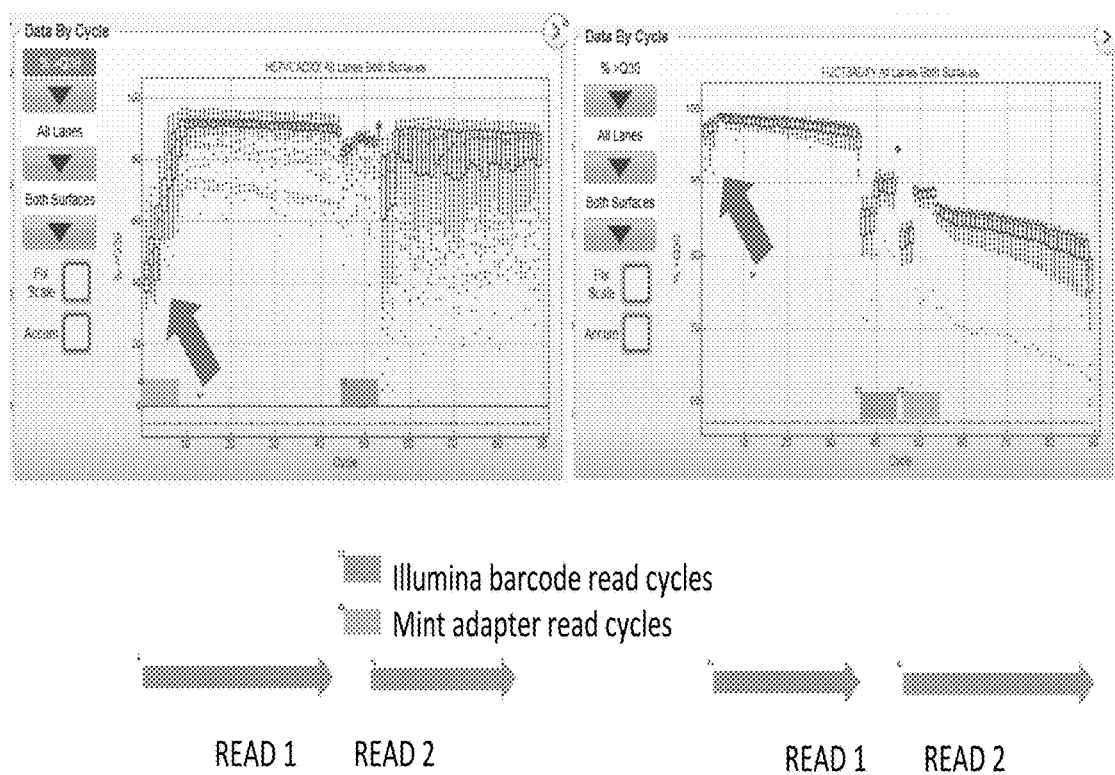
FIG. 26 provides a set of graphs showing the %>Q30 scores of the all cycles of sequencing using the standard (left) and inverted (right) adapter configurations. The standard adapter corresponds to FIG. 2 whereas the inverted adapter corresponds to FIG. 3.

FIG. 26 shows that the percent exceeding Q30 scores of the initial cycles using the inverse adapter were improved over those using the standard adapter. FIG. 27 demonstrates the impact of low quality initial read on sequencing. In particular, the results are consistent with the fact that in Illumina's technology, the quality of the first five cycles are critical to data quality overall. Use of the inverted adapter resulted in a higher success rate (97% perfect reads) of the PhiX control DNA than the standard adapter (51% perfect reads). FIG. 28 illustrates the percent of sequencing clusters passing a quality filter is significantly higher using the inverted adapter (97%) compared to the standard adapter (71%) and that the yield of reads passing filter is correspondingly higher using the inverse adapter (152 million reads passing filter) compared to the standard adapter (115 million reads passing filter). In spite of a similar cluster density between the two runs, the yield of passing filter reads is ⅓ higher using the inverted adapter.

The following tables provide example sequences used in accordance with certain embodiments disclosed herein.

TABLE 1

Sequences for the sense strand of double stranded adaptors. Underlined bases are the T7 promoter, the bases shown in bold text are the SBS12 sequence, and the bases shown in italics are the chromatin indexing barcode. The "Set ID" (SEQ ID NOs: 8-11) indicates a set of four barcodes that were optimized to work together such that each base is represented at each position of the barcode.

| Primer Name | Primer sequence, with 5' 3-carbon spacer, for the "sense" strand of the adapter | Set ID | SEQ ID NO |
|---|---|---|---|
| CBE103-Ad_BC03_s | /5SpC3/<u>GAATTTAATACGACTCACTATAGGAG</u>TTCAGACGTGTGCTCTTCCGATCT_ATACTTGG_ | | 1 |
| CBE104-Ad_BC04_s | /5SpC3/<u>GAATTTAATACGACTCACTATAGGAG</u>TTCAGACGTGTGCTCTTCCGATCT_CGCATTAG_ | | 2 |
| CBE111-Ad_BC11_s | /5SpC3/<u>GAATTTAATACGACTCACTATAGGAG</u>TTCAGACGTGTGCTCTTCCGATCT_ACTCTGGA_ | | 3 |
| CBE112-Ad_BC12_s | /5SpC3/<u>GAATTTAATACGACTCACTATAGGAG</u>TTCAGACGTGTGCTCTTCCGATCT_TGCGCAAT_ | | 4 |
| CBE114-Ad_BC14_s | /5SpC3/<u>GAATTTAATACGACTCACTATAGGAG</u>TTCAGACGTGTGCTCTTCCGATCT_GCAATTCG_ | | 5 |
| CBE116-Ad_BC16_s | /5SpC3/<u>GAATTTAATACGACTCACTATAGGAG</u>TTCAGACGTGTGCTCTTCCGATCT_TACCGGAT_ | | 6 |
| CBE117-Ad_BC17_s | /5SpC3/<u>GAATTTAATACGACTCACTATAGGAG</u>TTCAGACGTGTGCTCTTCCGATCT_CTGGAATC_ | | 7 |
| CBE122-Ad_BC22_s | /5SpC3/<u>GAATTTAATACGACTCACTATAGGAG</u>TTCAGACGTGTGCTCTTCCGATCT<u>CAGGTTAC</u> | SET1 | 8 |
| CBE123-Ad_BC23_s | /5SpC3/<u>GAATTTAATACGACTCACTATAGGAG</u>TTCAGACGTGTGCTCTTCCGATCT<u>GTAACCTG</u> | SET1 | 9 |
| CBE124-Ad_BC24_s | /5SpC3/<u>GAATTTAATACGACTCACTATAGGAG</u>TTCAGACGTGTGCTCTTCCGATCT<u>ACTTGGCA</u> | SET1 | 10 |
| CBE125-Ad_BC25_s | /5SpC3/<u>GAATTTAATACGACTCACTATAGGAG</u>TTCAGACGTGTGCTCTTCCGATCT<u>TGCCAAGT</u> | SET1 | 11 |
| CBE126-Ad_BC26_s | /5SpC3/<u>GAATTTAATACGACTCACTATAGGAG</u>TTCAGACGTGTGCTCTTCCGATCT_GCAGTACT_ | | 12 |

TABLE 2

PCR Primers.

| Forward primer name | Sequence | SEQ ID NO |
|---|---|---|
| PvG900-PCR_forward | AATGATACGGCGACCACCGAGATCTA*CACTCT* | 13 |
|  | TTCCCTACACGACGCTCTTCCGATCT |  |

| Reverse Primer names | | |
|---|---|---|
| CBE203-PCR_BC03 | CAAGCAGAAGACGGCATACGAGATAGATGTGC GTGACTGGAGTTCAGACGTGTGCTCTT | 14 |
| CBE204-PCR_BC04 | CAAGCAGAAGACGGCATACGAGATGTCGAGCA GTGACTGGAGTTCAGACGTGTGCTCTT | 15 |
| CBE209-PCR_BC09 | CAAGCAGAAGACGGCATACGAGATCAGTTGGT GTGACTGGAGTTCAGACGTGTGCTCTT | 16 |
| CBE210-PCR_BC10 | CAAGCAGAAGACGGCATACGAGATTCTGGACC GTGACTGGAGTTCAGACGTGTGCTCTT | 17 |
| CBE213-PCR_BC01 | CAAGCAGAAGACGGCATACGAGATCCTGGTAG GTGACTGGAGTTCAGACGTGTGCTCTT | 18 |
| CBE214-PCR_BC02 | CAAGCAGAAGACGGCATACGAGATTAAGCATG GTGACTGGAGTTCAGACGTGTGCTCTT | 19 |
| CBE215-PCR_BC05 | CAAGCAGAAGACGGCATACGAGATGAATTGCT GTGACTGGAGTTCAGACGTGTGCTCTT | 20 |
| CBE216-PCR_BC06 | CAAGCAGAAGACGGCATACGAGATTCGCACCT GTGACTGGAGTTCAGACGTGTGCTCTT | 21 |
| CBE217-PCR_BC07 | CAAGCAGAAGACGGCATACGAGATCTAACTGG GTGACTGGAGTTCAGACGTGTGCTCTT | 22 |
| CBE218-PCR_BC08 | CAAGCAGAAGACGGCATACGAGATAGGCTCAA GTGACTGGAGTTCAGACGTGTGCTCTT | 23 |
| CBE219-PCR_BC11 | CAAGCAGAAGACGGCATACGAGATTGTTATAC GTGACTGGAGTTCAGACGTGTGCTCTT | 24 |
| CBE220-PCR_BC12 | CAAGCAGAAGACGGCATACGAGATTCAGCGAA GTGACTGGAGTTCAGACGTGTGCTCTT | 25 |

In the forward primer, the P5 primer is shown in underlining; the sequence shown in bold text (GATCT) is a 5-bp spacer/linker sequence; and the sequence shown in italics is the inverse complement of the sequence of SBS3.
In the reverse primers, the Illumina P7 primer is shown in underlining; the 3 bp shown in bold text (GAT) are a spacer/linker sequence; the inverse complement of the Illumina barcode is shown in italics, which is used for demultiplexing the antibody used in ChIP; and the 27 bases at the 5' end of SBS12 are shown in highlighting.

In addition, a random primer was used in inverse reactions, which had the following sequence: CBE100-SBS3-RT: TACACGACGCTCTTCCGATCTNNNNNN (SEQ ID NO:35).

As shown in Table 3, three phosphorothioate linkages were added between the ultimate 4 bases of the "sense" strand of the oligo, indicated by the asterisks. The sense strands are shown drawn in the conventional 5' to 3' direction. The adapter barcode used for chromatin demultiplexing is indicated by underlining. The name of the adapter sequence reflects its modified chemistry (i.e., PT3 indicates the 3 phosphorothioate linkages).

In the case of primer CBE135.PT3-Ad_BC35_s (SEQ ID NO:26), the sequence of the "anti-sense" strand, together with its chemical modifications, is provided as SEQ ID NO:27. These modifications are incorporated into all of the anti-sense strand designs, but for simplicity, they are only shown once here in connection with a particular design. In the case of the "anti-sense" strand, it is written in the non-conventional 3' to 5' direction, in order to highlight the Watson-Crick base-pairing with the sense strand. The new designs incorporate a number of elements in the sequence of the anti-sense strand, including: (1) three phosphorothioate linkages between the initial four bases, indicated by asterisks; (2) a 5' phosphate modification on the initial base of the antisense strand of all chromatin adapters. The name of the adapter sequence reflects its modified chemistry (i.e., PT3 indicates the 3 phosphorothioate linkages, and the "P" refers to the 5' Phosphate).

TABLE 3

Sequences for the sense strand of the double stranded adaptor barcodes with phosphorothioate linkages indicated by the asterisks.

| Primer Name | Primer sequence, with 5' 3-carbon spacer, for the "sense" strand of the adapter | SEQ ID NO |
|---|---|---|
| CBE135.PT3-Ad_BC35_s | /5SpC3/GAATTTAATACGACTCACTATAGGAGT TCAGACGTGTGCTCTTCCGATCTGCCAT*G*A*T | 26 |
| CBE135P.PT3-Ad_BC35_as | CTTAAATTATGCTGAGTGATATCCTCAAGTCTGC ACACGAGAAGGCTAGACGGTA*C*T*A/5Phos/ | 27 |
| CBE136.PT3-Ad_BC36_s | /5SpC3/GAATTTAATACGACTCACTATAGGAGT TCAGACGTGTGCTCTTCCGATCTAGGTC*A*T*C | 28 |
| CBE139.PT3-Ad_BC39_s | /5SpC3/GAATTTAATACGACTCACTATAGGAGT TCAGACGTGTGCTCTTCCGATCTAGCTG*C*A*T | 29 |
| CBE142.PT3-Ad_BC42_s | /5SpC3/GAATTTAATACGACTCACTATAGGAGT TCAGACGTGTGCTCTTCCGATCTTCGGA*T*C*A | 30 |

TABLE 3-continued

Sequences for the sense strand of the double stranded adaptor barcodes with phosphorothioate linkages indicated by the asterisks.

| Primer Name | Primer sequence, with 5' 3-carbon spacer, for the "sense" strand of the adapter | SEQ ID NO |
|---|---|---|
| CBE143.PT3-Ad_BC43_s | /5SpC3/GAATTTAATACGACTCACTATAGGAGTTCAGACGTGTGCTCTTCCGATCTCGAAT*C*G*T | 31 |
| CBE147.PT3-Ad_BC47_s | /5SpC3/GAATTTAATACGACTCACTATAGGAGTTCAGACGTGTGCTCTTCCGATCTCACTG*G*A*T | 32 |
| CBE152.PT3-Ad_BC52_s | /5SpC3/GAATTTAATACGACTCACTATAGGAGTTCAGACGTGTGCTCTTCCGATCTTGAGT*C*A*C | 33 |
| CBE155.PT3-Ad_BC55_s | /5SpC3/GAATTTAATACGACTCACTATAGGAGTTCAGACGTGTGCTCTTCCGATCTTACGG*C*A*T | 34 |

Various modifications and variations of the described methods, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for labeling nucleic acids from a cell or population of cells comprising:
   providing one or more individual discrete volumes, each individual discrete volume comprising a cell or population of cells;
   lysing the cell or population of cells in each individual discrete volume and fragmenting nucleosomal DNA from the lysed cell or population of cells;
   labeling the fragmented nucleosomal DNA in each individual discrete volume with a barcoded adapter on at least one free end of the fragmented nucleosomal DNA, wherein:
   the barcoded adapter comprises an amplification promoter adjacent to a first or second read sequencing primer binding site which is adjacent to a barcode sequence,
   the labeled nucleosomal DNA comprises, in a 3' to 5' orientation, a first read sequencing primer binding site, the nucleosomal DNA sequence, the barcode sequence, and a second read sequencing primer binding site,
   the barcode sequence is unique to each individual discrete volume thereby identifying a sample from which the labeled nucleosomal DNA originated;
   isolating and sequencing the labeled nucleosomal DNA from each sample; and
   grouping the sequenced nucleosomal DNA by common barcode thereby identifying the individual discrete volumes from which the nucleosomal DNA originated.

2. The method of claim 1, wherein sequencing the labeled nucleosomal DNA comprises:
   generating amplified RNA copies of the labeled nucleosomal DNA by in vitro transcription from the amplification promoter on the barcoded adapter;
   generating cDNA from the amplified RNA copies using a reverse transcription primer comprising a random hexamer and a second sequencing primer binding site; and
   generating a dsDNA copy of the cDNA for sequencing by amplification using an amplification primer pair, and each primer in an amplification primer pair comprising a sequencing primer binding site and sequencing adapter, wherein the resulting dsDNA copy incorporates the first and second read sequencing primer binding sites and a sequencing adapter on both ends of the dsDNA copy.

3. The method of claim 2, wherein the primer pair used on each sample incorporates a second barcode during amplification that identifies the nucleosomal modification detected by the nucleosomal modification detection assay performed on that assay sample.

4. The method of claim 2, wherein the first sequencing primer binding site of the adapter is a first read sequencing primer binding site, and the second sequencing primer binding site on the reverse transcription primer is a second read sequencing primer binding site.

5. The method of claim 1, further comprising conducting one or more nucleosomal modification detection assays on each individual discrete volume, wherein grouping the sequenced nucleosomal DNA by common barcode further identifies epigenetic modifications in the cell or population of cells in each individual discrete volume.

6. The method of claim 5, wherein the one or more nucleosomal modification detection assay is a chromatin immunoprecipitation assay.

7. The method of claim 6, wherein the chromatin immunoprecipitation assay detects one or more chemical modifications of histones.

8. The method of claim 5, further comprising pooling all labeled nucleosomal DNA and then splitting the nucleosomal DNA into separate assay samples for each nucleosomal modification detection assay to be conducted.

9. The method of claim 1, wherein the barcoded adapter is double-stranded.

10. The method of claim 1, wherein digestion of the nucleosomal DNA is done using a micrococcal nuclease (MNase).

11. The method of claim 1, wherein the individual discrete volume is an individual reaction tube or well of a microwell plate.

12. The method of claim 1, wherein the individual discrete volume is a droplet generated on a microfluidic device.

13. The method of claim 1, wherein labeling the fragmented nucleosomal DNA in each individual discrete volume with barcoded adapters comprises delivering to each individual discrete volume a unique set of barcoded adapters, wherein all barcoded adapters in the set identify the individual discrete volume and each individual barcoded adapter in a given set comprises a unique barcode sequence.

14. The method of claim 13, wherein the set comprises four adapters wherein each individual adapter in the set comprises a unique barcode sequence such that between the four adapters the nucleosides adenine, guanine, cytosine, or thymine are represented at each position in one of the adapter barcode sequences.

* * * * *

SEQUENCE LISTING

<160> NUMBER OF SEQ ID NOS: 35

<210> SEQ ID NO 1
<211> LENGTH: 58
<212> TYPE: DNA
<213> ORGANISM: Artificial Sequence
<220> FEATURE:
<223> OTHER INFORMATION: Synthetic

<400> SEQUENCE: 1
gaatttaata cgactcacta taggagttca gacgtgtgct cttccgatct atacttgg      58

<210> SEQ ID NO 2
<211> LENGTH: 58
<212> TYPE: DNA
<213> ORGANISM: Artificial
<220> FEATURE:
<223> OTHER INFORMATION: Synthetic

<400> SEQUENCE: 2
gaatttaata cgactcacta taggagttca gacgtgtgct cttccgatct cgcattag      58

<210> SEQ ID NO 3
<211> LENGTH: 58
<212> TYPE: DNA
<213> ORGANISM: Artificial
<220> FEATURE:
<223> OTHER INFORMATION: Synthetic

<400> SEQUENCE: 3
gaatttaata cgactcacta taggagttca gacgtgtgct cttccgatct actctgga      58

<210> SEQ ID NO 4
<211> LENGTH: 58
<212> TYPE: DNA
<213> ORGANISM: Artificial
<220> FEATURE:
<223> OTHER INFORMATION: Synthetic

<400> SEQUENCE: 4
gaatttaata cgactcacta taggagttca gacgtgtgct cttccgatct tgcgcaat      58

<210> SEQ ID NO 5
<211> LENGTH: 58

```
<212> TYPE: DNA
<213> ORGANISM: Artificial
<220> FEATURE:
<223> OTHER INFORMATION: Synthetic

<400> SEQUENCE: 5
gaatttaata cgactcacta taggagttca gacgtgtgct cttccgatct gcaattcg      58

<210> SEQ ID NO 6
<211> LENGTH: 58
<212> TYPE: DNA
<213> ORGANISM: Artificial
<220> FEATURE:
<223> OTHER INFORMATION: Synthetic

<400> SEQUENCE: 6
gaatttaata cgactcacta taggagttca gacgtgtgct cttccgatct taccggat      58

<210> SEQ ID NO 7
<211> LENGTH: 58
<212> TYPE: DNA
<213> ORGANISM: Artificial
<220> FEATURE:
<223> OTHER INFORMATION: Synthetic

<400> SEQUENCE: 7
gaatttaata cgactcacta taggagttca gacgtgtgct cttccgatct ctggaatc      58

<210> SEQ ID NO 8
<211> LENGTH: 58
<212> TYPE: DNA
<213> ORGANISM: Artificial
<220> FEATURE:
<223> OTHER INFORMATION: Synthetic

<400> SEQUENCE: 8
gaatttaata cgactcacta taggagttca gacgtgtgct cttccgatct caggttac      58

<210> SEQ ID NO 9
<211> LENGTH: 58
<212> TYPE: DNA
<213> ORGANISM: Artificial
<220> FEATURE:
<223> OTHER INFORMATION: Synthetic

<400> SEQUENCE: 9
gaatttaata cgactcacta taggagttca gacgtgtgct cttccgatct gtaacctg      58

<210> SEQ ID NO 10
<211> LENGTH: 58
<212> TYPE: DNA
<213> ORGANISM: Artificial
<220> FEATURE:
<223> OTHER INFORMATION: Synthetic

<400> SEQUENCE: 10
gaatttaata cgactcacta taggagttca gacgtgtgct cttccgatct acttggca      58

<210> SEQ ID NO 11
<211> LENGTH: 58
<212> TYPE: DNA
<213> ORGANISM: Artificial
<220> FEATURE:
<223> OTHER INFORMATION: Synthetic

<400> SEQUENCE: 11
```
gaatttaata cgactcacta taggagttca gacgtgtgct cttccgatct tgccaagt    58

<210> SEQ ID NO 12
<211> LENGTH: 58
<212> TYPE: DNA
<213> ORGANISM: Artificial
<220> FEATURE:
<223> OTHER INFORMATION: Synthetic

<400> SEQUENCE: 12
gaatttaata cgactcacta taggagttca gacgtgtgct cttccgatct gcagtact    58

<210> SEQ ID NO 13
<211> LENGTH: 58
<212> TYPE: DNA
<213> ORGANISM: Artificial
<220> FEATURE:
<223> OTHER INFORMATION: Synthetic

<400> SEQUENCE: 13
aatgatacgg cgaccaccga gatctacact ctttccctac acgacgctct tccgatct    58

<210> SEQ ID NO 14
<211> LENGTH: 59
<212> TYPE: DNA
<213> ORGANISM: Artificial
<220> FEATURE:
<223> OTHER INFORMATION: Synthetic

<400> SEQUENCE: 14
caagcagaag acggcatacg agatagatgt gcgtgactgg agttcagacg tgtgctctt    59

<210> SEQ ID NO 15
<211> LENGTH: 59
<212> TYPE: DNA
<213> ORGANISM: Artificial
<220> FEATURE:
<223> OTHER INFORMATION: Synthetic

<400> SEQUENCE: 15
caagcagaag acggcatacg agatgtcgag cagtgactgg agttcagacg tgtgctctt    59

<210> SEQ ID NO 16
<211> LENGTH: 59
<212> TYPE: DNA
<213> ORGANISM: Artificial
<220> FEATURE:
<223> OTHER INFORMATION: Synthetic

<400> SEQUENCE: 16
caagcagaag acggcatacg agatcagttg gtgtgactgg agttcagacg tgtgctctt    59

<210> SEQ ID NO 17
<211> LENGTH: 59
<212> TYPE: DNA
<213> ORGANISM: Artificial
<220> FEATURE:
<223> OTHER INFORMATION: Synthetic

<400> SEQUENCE: 17
caagcagaag acggcatacg agattctgga ccgtgactgg agttcagacg tgtgctctt    59

<210> SEQ ID NO 18
<211> LENGTH: 59
<212> TYPE: DNA
<213> ORGANISM: Artificial

<220> FEATURE:
<223> OTHER INFORMATION: Synthetic

<400> SEQUENCE: 18
caagcagaag acggcatacg agatcctggt aggtgactgg agttcagacg tgtgctctt      59

<210> SEQ ID NO 19
<211> LENGTH: 59
<212> TYPE: DNA
<213> ORGANISM: Artificial
<220> FEATURE:
<223> OTHER INFORMATION: Synthetic

<400> SEQUENCE: 19
caagcagaag acggcatacg agattaagca tggtgactgg agttcagacg tgtgctctt      59

<210> SEQ ID NO 20
<211> LENGTH: 59
<212> TYPE: DNA
<213> ORGANISM: Artificial
<220> FEATURE:
<223> OTHER INFORMATION: Synthetic

<400> SEQUENCE: 20
caagcagaag acggcatacg agatgaattg ctgtgactgg agttcagacg tgtgctctt      59

<210> SEQ ID NO 21
<211> LENGTH: 59
<212> TYPE: DNA
<213> ORGANISM: Artificial
<220> FEATURE:
<223> OTHER INFORMATION: Synthetic

<400> SEQUENCE: 21
caagcagaag acggcatacg agattcgcac ctgtgactgg agttcagacg tgtgctctt      59

<210> SEQ ID NO 22
<211> LENGTH: 59
<212> TYPE: DNA
<213> ORGANISM: Artificial
<220> FEATURE:
<223> OTHER INFORMATION: Synthetic

<400> SEQUENCE: 22
caagcagaag acggcatacg agatctaact gggtgactgg agttcagacg tgtgctctt      59

<210> SEQ ID NO 23
<211> LENGTH: 59
<212> TYPE: DNA
<213> ORGANISM: Artificial
<220> FEATURE:
<223> OTHER INFORMATION: Synthetic

<400> SEQUENCE: 23
caagcagaag acggcatacg agataggctc aagtgactgg agttcagacg tgtgctctt      59

<210> SEQ ID NO 24
<211> LENGTH: 59
<212> TYPE: DNA
<213> ORGANISM: Artificial
<220> FEATURE:
<223> OTHER INFORMATION: Synthetic

<400> SEQUENCE: 24
caagcagaag acggcatacg agattgttat acgtgactgg agttcagacg tgtgctctt      59

```
<210> SEQ ID NO 25
<211> LENGTH: 59
<212> TYPE: DNA
<213> ORGANISM: Artificial
<220> FEATURE:
<223> OTHER INFORMATION: Synthetic

<400> SEQUENCE: 25
caagcagaag acggcatacg agattcagcg aagtgactgg agttcagacg tgtgctctt      59

<210> SEQ ID NO 26
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 26
gaatttaata cgactcacta taggagttca gacgtgtgct cttccgatct gccatgat       58

<210> SEQ ID NO 27
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 27
cttaaattat gctgagtgat atcctcaagt ctgcacacga aaggctaga cggtacta        58

<210> SEQ ID NO 28
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
```

```
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 28
gaatttaata cgactcacta taggagttca gacgtgtgct cttccgatct aggtcatc      58

<210> SEQ ID NO 29
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 29
gaatttaata cgactcacta taggagttca gacgtgtgct cttccgatct agctgcat      58

<210> SEQ ID NO 30
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 30
gaatttaata cgactcacta taggagttca gacgtgtgct cttccgatct tcggatca      58

<210> SEQ ID NO 31
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
``` nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 31
gaatttaata cgactcacta taggagttca gacgtgtgct cttccgatct cgaatcgt    58

<210> SEQ ID NO 32
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 32
gaatttaata cgactcacta taggagttca gacgtgtgct cttccgatct cactggat    58

<210> SEQ ID NO 33
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 33
gaatttaata cgactcacta taggagttca gacgtgtgct cttccgatct tgagtcac    58

<210> SEQ ID NO 34
<211> LENGTH: 58
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature

```
<222> LOCATION: (55)..(56)
<223> OTHER INFORMATION: A phosphorothioate linkage exists between
      nucleotides 55 and 56
<220> FEATURE:
<221> NAME/KEY: misc_feature
<222> LOCATION: (56)..(57)
<223> OTHER INFORMATION: A phosphorothioate linkage exists between
      nucleotides 55 and 56
<220> FEATURE:
<221> NAME/KEY: misc_feature
<222> LOCATION: (57)..(58)
<223> OTHER INFORMATION: A phosphorothioate linkage exists between
      nucleotides 55 and 56

<400> SEQUENCE: 34
gaatttaata cgactcacta taggagttca gacgtgtgct cttccgatct tacggcat          58

<210> SEQ ID NO 35
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (22)..(27)
<223> OTHER INFORMATION: n is a, c, g, or t

<400> SEQUENCE: 35
tacacgacgc tcttccgatc tnnnnnn                                            27
```